(12) United States Patent
Ferguson et al.

(10) Patent No.: US 8,226,617 B2
(45) Date of Patent: Jul. 24, 2012

(54) SAFETY SHIELD APPARATUS AND MOUNTING STRUCTURE FOR USE WITH MEDICAL NEEDLE DEVICES

(75) Inventors: F. Mark Ferguson, Salt Lake City, UT (US); Eugene E. Weilbacher, Chesterfield, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 341 days.

(21) Appl. No.: 11/716,502

(22) Filed: Mar. 8, 2007

(65) Prior Publication Data

US 2007/0282275 A1 Dec. 6, 2007

Related U.S. Application Data

(63) Continuation-in-part of application No. 09/892,593, filed on Jun. 27, 2001, now Pat. No. 7,198,618, which is a continuation-in-part of application No. 09/433,449, filed on Nov. 4, 1999, now Pat. No. 6,280,420, and a continuation-in-part of application No. 09/434,036, filed on Nov. 4, 1999, now Pat. No. 6,254,575, and a continuation-in-part of application No. 09/619,190, filed on Jul. 19, 2000, now Pat. No. 6,592,556.

(60) Provisional application No. 60/254,506, filed on Dec. 8, 2000, provisional application No. 60/275,810, filed on Mar. 14, 2001, provisional application No. 60/275,886, filed on Mar. 14, 2001, provisional application No. 60/296,968, filed on Jun. 8, 2001, provisional application No. 60/794,978, filed on Apr. 26, 2006.

(51) Int. Cl.
*A61M 5/32* (2006.01)

(52) U.S. Cl. ........................................ 604/192; 604/198
(58) Field of Classification Search .................. 604/192, 604/198, 263
See application file for complete search history.

(56) References Cited

U.S. PATENT DOCUMENTS 1,779,451 A 10/1930 Sponsel
(Continued)

FOREIGN PATENT DOCUMENTS

EP 0 144 483 A3 6/1985
(Continued)

OTHER PUBLICATIONS

Office action issued May 26, 2011 in related U.S. Appl. No. 12/836,622, 7 pgs.

(Continued)

*Primary Examiner* — Kevin C Sirmons
*Assistant Examiner* — Brandy C Scott
(74) *Attorney, Agent, or Firm* — Lisa E. Winsor, Esq.

(57) ABSTRACT

A safety shield apparatus including a safety shield and mounting structure for mounting the safety shield to a medical needle. The safety shield includes a distal segment, a proximal segment and a retention member. The distal segment is pivotally secured to the proximal segment and the proximal segment is pivotally secured to the retention member. The retention member includes an opening for receiving a nose of a medical needle device, e.g., a blood collection device. In one embodiment, a retaining collar is provided which is dimensioned to be press-fit about the nose of the medical needle device to secure the safety shield to the medical needle device. Alternatively, mounting structure is formed directly on the retention member to secure the safety shield to the medical needle device.

19 Claims, 18 Drawing Sheets

U.S. PATENT DOCUMENTS

| | | | |
|---|---|---|---|
| 2,559,474 A | 7/1951 | Son | |
| 2,700,385 A | 1/1955 | Ortiz | |
| 2,836,942 A | 6/1958 | Miskel | |
| 2,854,976 A | 10/1958 | Heydrich | |
| 2,953,243 A | 9/1960 | Roehr | |
| 3,021,942 A | 2/1962 | Hamilton | |
| 3,073,307 A | 1/1963 | Stevens | |
| 3,074,542 A | 1/1963 | Myerson et al. | |
| 3,255,873 A | 6/1966 | Speelman | |
| 3,294,231 A | 12/1966 | Vanderbeck | |
| 3,323,523 A | 6/1967 | Scislowicz et al. | |
| 3,329,146 A | 7/1967 | Waldman, Jr. | |
| 3,333,682 A | 8/1967 | Burke | |
| 3,367,488 A | 2/1968 | Hamilton | |
| 3,485,239 A | 12/1969 | Vanderbeck | |
| 3,537,452 A | 11/1970 | Wilks | |
| 3,587,575 A | 6/1971 | Lichtenstein | |
| 3,610,240 A | 10/1971 | Harautuneian | |
| 3,658,061 A | 4/1972 | Hall | |
| 3,828,775 A | 8/1974 | Armel | |
| 3,840,008 A | 10/1974 | Noiles | |
| 3,890,971 A | 6/1975 | Leeson et al. | |
| 3,904,033 A | 9/1975 | Haerr | |
| 3,934,722 A | 1/1976 | Goldberg | |
| 3,968,876 A | 7/1976 | Brookfield | |
| 4,040,419 A | 8/1977 | Goldman | |
| 4,106,621 A | 8/1978 | Sorenson | |
| 4,113,090 A | 9/1978 | Carstens | |
| 4,139,009 A | 2/1979 | Alvarez | |
| 4,175,008 A | 11/1979 | White | |
| 4,270,536 A | 6/1981 | Lemelson | |
| 4,300,678 A | 11/1981 | Gyure et al. | |
| 4,375,849 A | 3/1983 | Hanifl | |
| 4,430,082 A | 2/1984 | Schwabacher | |
| 4,592,744 A | 6/1986 | Jagger et al. | |
| 4,634,428 A | 1/1987 | Cuu | |
| 4,643,722 A | 2/1987 | Smith, Jr. | |
| 4,659,330 A | 4/1987 | Nelson et al. | |
| 4,664,259 A | 5/1987 | Landis | |
| 4,664,654 A | 5/1987 | Strauss | |
| 4,681,567 A | 7/1987 | Masters et al. | |
| 4,695,274 A | 9/1987 | Fox | |
| 4,702,738 A | 10/1987 | Spencer | |
| 4,723,943 A | 2/1988 | Spencer | |
| 4,728,320 A | 3/1988 | Chen | |
| 4,728,321 A | 3/1988 | Chen | |
| 4,731,059 A | 3/1988 | Wanderer et al. | |
| 4,735,311 A | 4/1988 | Lowe et al. | |
| 4,735,618 A | 4/1988 | Hagen | |
| 4,737,144 A | 4/1988 | Choksi | |
| 4,738,663 A | 4/1988 | Bogan | |
| 4,743,233 A | 5/1988 | Schneider | |
| 4,747,836 A | 5/1988 | Luther | |
| 4,747,837 A | 5/1988 | Hauck | |
| 4,772,272 A | 9/1988 | McFarland | |
| 4,778,453 A | 10/1988 | Lopez | |
| 4,781,697 A | 11/1988 | Slaughter | |
| 4,782,841 A | 11/1988 | Lopez | |
| 4,790,828 A | 12/1988 | Dombrowski et al. | |
| 4,795,432 A | 1/1989 | Karczmer | |
| 4,795,443 A | 1/1989 | Permenter et al. | |
| 4,801,295 A | 1/1989 | Spencer | |
| 4,804,372 A | 2/1989 | Laico et al. | |
| 4,813,426 A | 3/1989 | Haber et al. | |
| 4,816,022 A | 3/1989 | Poncy | |
| 4,816,024 A | 3/1989 | Sitar et al. | |
| 4,819,659 A | 4/1989 | Sitar | |
| 4,820,277 A | 4/1989 | Norelli | |
| 4,826,490 A | 5/1989 | Byrne et al. | |
| 4,826,491 A | 5/1989 | Schramm | |
| 4,838,871 A | 6/1989 | Luther | |
| 4,840,619 A | 6/1989 | Hughes | |
| 4,842,587 A | 6/1989 | Poncy | |
| 4,846,796 A | 7/1989 | Carrell et al. | |
| 4,846,811 A | 7/1989 | Vanderhoof | |
| 4,850,968 A | 7/1989 | Romano | |
| 4,850,976 A | 7/1989 | Heinrich et al. | |
| 4,850,977 A | 7/1989 | Bayless | |
| 4,850,978 A | 7/1989 | Dudar et al. | |
| 4,850,994 A | 7/1989 | Zerbst et al. | |
| 4,850,996 A | 7/1989 | Cree | |
| 4,858,607 A | 8/1989 | Jordan et al. | |
| 4,863,434 A | 9/1989 | Bayless | |
| 4,863,435 A | 9/1989 | Sturman et al. | |
| 4,863,436 A | 9/1989 | Glick | |
| 4,867,172 A | 9/1989 | Haber et al. | |
| 4,867,746 A | 9/1989 | Dufresne | |
| 4,872,552 A | 10/1989 | Unger | |
| 4,874,382 A | 10/1989 | Lindemann et al. | |
| 4,874,383 A | 10/1989 | McNaughton | |
| 4,874,384 A | 10/1989 | Nunez | |
| 4,883,469 A | 11/1989 | Glazier | |
| 4,886,503 A | 12/1989 | Miller | |
| 4,887,998 A | 12/1989 | Martin et al. | |
| 4,888,001 A | 12/1989 | Schoenberg | |
| 4,892,107 A | 1/1990 | Haber | |
| 4,892,521 A | 1/1990 | Laico et al. | |
| 4,898,589 A | 2/1990 | Dolgin et al. | |
| 4,900,309 A | 2/1990 | Netherton et al. | |
| 4,904,244 A | 2/1990 | Harsh et al. | |
| 4,911,694 A | 3/1990 | Dolan | |
| 4,911,706 A | 3/1990 | Levitt | |
| 4,915,697 A | 4/1990 | DuPont | |
| 4,927,018 A | 5/1990 | Yang et al. | |
| 4,929,241 A | 5/1990 | Kulli | |
| 4,935,012 A | 6/1990 | Magre et al. | |
| 4,935,013 A | 6/1990 | Haber et al. | |
| 4,936,830 A | 6/1990 | Verlier | |
| 4,944,397 A | 7/1990 | Miller | |
| 4,944,731 A | 7/1990 | Cole | |
| 4,950,249 A | 8/1990 | Jagger et al. | |
| 4,950,250 A | 8/1990 | Haber et al. | |
| 4,978,344 A | 12/1990 | Dombrowski et al. | |
| 4,982,842 A | 1/1991 | Hollister | |
| 4,985,021 A | 1/1991 | Straw et al. | |
| 4,994,041 A | 2/1991 | Dombrowski et al. | |
| 5,000,744 A | 3/1991 | Hoffman et al. | |
| 5,015,240 A | 5/1991 | Soproni et al. | |
| 5,057,089 A | 10/1991 | Greco | |
| 5,059,180 A | 10/1991 | McLees | |
| 5,092,851 A | 3/1992 | Ragner | |
| 5,108,379 A | 4/1992 | Dolgin et al. | |
| RE34,045 E | 8/1992 | McFarland | |
| 5,135,509 A * | 8/1992 | Olliffe | 604/192 |
| 5,139,489 A | 8/1992 | Hollister | |
| 5,147,303 A | 9/1992 | Martin | |
| 5,154,285 A | 10/1992 | Hollister | |
| 5,176,655 A | 1/1993 | McCormick et al. | |
| 5,176,656 A | 1/1993 | Bayless | |
| 5,188,611 A | 2/1993 | Orgain | |
| 5,193,552 A | 3/1993 | Columbus et al. | |
| 5,195,983 A | 3/1993 | Boese | |
| 5,209,739 A | 5/1993 | Talalay | |
| 5,232,454 A | 8/1993 | Hollister | |
| 5,232,455 A | 8/1993 | Hollister | |
| 5,242,417 A | 9/1993 | Paudler | |
| 5,242,418 A | 9/1993 | Weinstein | |
| 5,246,427 A | 9/1993 | Sturman et al. | |
| 5,246,428 A | 9/1993 | Falknor | |
| 5,250,031 A | 10/1993 | Kaplan et al. | |
| 5,254,099 A | 10/1993 | Kuracina et al. | |
| 5,256,152 A | 10/1993 | Marks | |
| 5,256,153 A | 10/1993 | Hake | |
| 5,277,311 A | 1/1994 | Hollister | |
| 5,290,255 A | 3/1994 | Vallelunga et al. | |
| 5,304,137 A | 4/1994 | Fluke | |
| 5,312,369 A | 5/1994 | Arcusin et al. | |
| 5,334,158 A | 8/1994 | McLees | |
| 5,348,544 A * | 9/1994 | Sweeney et al. | 604/192 |
| 5,356,392 A | 10/1994 | Firth et al. | |
| 5,403,283 A | 4/1995 | Luther | |
| 5,403,286 A | 4/1995 | Lockwood, Jr. | |
| 5,407,436 A | 4/1995 | Toft et al. | |
| 5,411,492 A | 5/1995 | Sturman et al. | |
| 5,423,765 A | 6/1995 | Hollister | |
| 5,423,766 A | 6/1995 | Di Cesare | |
| 5,425,720 A | 6/1995 | Rogalsky et al. | |

| Patent Number | Date | Inventor |
|---|---|---|
| 5,447,501 A | 9/1995 | Karlsson et al. |
| 5,466,223 A | 11/1995 | Bressler et al. |
| 5,480,385 A | 1/1996 | Thorne et al. |
| 5,487,733 A | 1/1996 | Caizza et al. |
| 5,487,734 A | 1/1996 | Thorne et al. |
| 5,490,841 A | 2/1996 | Landis |
| 5,498,243 A | 3/1996 | Vallelunga et al. |
| 5,531,694 A | 7/1996 | Clemens et al. |
| 5,533,980 A | 7/1996 | Sweeney et al. |
| 5,538,508 A | 7/1996 | Steyn |
| 5,542,927 A | 8/1996 | Thorne et al. |
| 5,549,568 A | 8/1996 | Shields |
| 5,549,570 A | 8/1996 | Rogalsky |
| 5,549,708 A | 8/1996 | Thorne et al. |
| 5,562,629 A | 10/1996 | Haughton et al. |
| 5,562,631 A | 10/1996 | Bogert |
| 5,573,510 A | 11/1996 | Isaacson |
| 5,584,816 A | 12/1996 | Gyure et al. |
| 5,584,818 A | 12/1996 | Morrison |
| 5,599,313 A * | 2/1997 | Gyure et al. .......... 604/192 |
| 5,599,318 A | 2/1997 | Sweeney et al. |
| 5,611,782 A | 3/1997 | Haedt |
| 5,643,220 A | 7/1997 | Cosme |
| 5,665,075 A | 9/1997 | Gyure et al. |
| 5,672,161 A | 9/1997 | Allen et al. |
| 5,695,474 A | 12/1997 | Daugherty |
| 5,695,477 A | 12/1997 | Sfikas |
| 5,700,249 A | 12/1997 | Jenkins |
| 5,735,827 A | 4/1998 | Adwers et al. |
| 5,738,665 A | 4/1998 | Caizza et al. |
| 5,746,718 A | 5/1998 | Steyn |
| 5,746,726 A | 5/1998 | Sweeney et al. |
| 5,755,699 A | 5/1998 | Blecher et al. |
| 5,807,351 A * | 9/1998 | Kashmer .......... 604/263 |
| 5,814,018 A | 9/1998 | Elson et al. |
| 5,817,064 A | 10/1998 | DeMarco et al. |
| 5,823,997 A | 10/1998 | Thorne |
| 5,843,041 A | 12/1998 | Hake et al. |
| 5,910,130 A | 6/1999 | Caizza et al. |
| 5,919,168 A | 7/1999 | Wheeler |
| 5,925,020 A | 7/1999 | Nestell |
| 5,951,522 A | 9/1999 | Rosato et al. |
| 5,951,525 A | 9/1999 | Thorne et al. |
| 5,957,892 A | 9/1999 | Thorne |
| 5,980,488 A | 11/1999 | Thorne |
| 6,015,397 A * | 1/2000 | Elson et al. .......... 604/192 |
| 6,036,675 A | 3/2000 | Thorne et al. |
| 6,149,629 A | 11/2000 | Wilson et al. |
| 6,171,284 B1 | 1/2001 | Kao et al. |
| RE37,110 E | 3/2001 | Hollister |
| 6,224,576 B1 | 5/2001 | Thorne et al. |
| RE37,252 E | 7/2001 | Hollister |
| 6,254,575 B1 | 7/2001 | Thorne, Jr. et al. |
| 6,280,420 B1 | 8/2001 | Ferguson et al. |
| 6,298,541 B1 * | 10/2001 | Newby et al. .......... 29/458 |
| 6,334,857 B1 | 1/2002 | Hollister et al. |
| 6,582,397 B2 | 6/2003 | Alesi et al. |
| 6,592,556 B1 | 7/2003 | Thorne |
| 6,796,968 B2 | 9/2004 | Ferguson et al. |
| 6,949,086 B2 | 9/2005 | Ferguson et al. |
| 7,029,461 B2 | 4/2006 | Ferguson et al. |
| 7,144,389 B2 | 12/2006 | Ferguson et al. |
| 7,198,618 B2 | 4/2007 | Ferguson et al. |
| 2001/0039401 A1 | 11/2001 | Ferguson et al. |
| 2002/0004650 A1 | 1/2002 | Kuracina et al. |
| 2002/0072716 A1 | 6/2002 | Barrus et al. |
| 2003/0004465 A1 | 1/2003 | Ferguson et al. |
| 2003/0088215 A1 | 5/2003 | Ferguson et al. |
| 2003/0229317 A1 | 12/2003 | Ferguson et al. |

FOREIGN PATENT DOCUMENTS

| | | |
|---|---|---|
| EP | 0 344 606 B1 | 12/1989 |
| EP | 0 457 477 B1 | 11/1991 |
| EP | 0 485 345 B1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 B1 | 1/1998 |
| EP | 0 815 890 B1 | 1/1998 |
| EP | 0 819 441 A1 | 1/1998 |
| EP | 0 832 659 B1 | 4/1998 |
| EP | 0 832 660 A2 | 4/1998 |
| EP | 1 092 443 A2 | 4/2001 |
| EP | 1 116 493 A1 | 7/2001 |
| GB | 1 233 302 | 5/1971 |
| GB | 2 283 429 | 5/1995 |
| GB | 2 369 779 | 6/2002 |
| JP | 10-76007 | 3/1998 |
| JP | 10-127765 | 5/1998 |
| WO | WO 87/07162 A1 | 12/1987 |
| WO | WO 89/07955 A1 | 9/1989 |
| WO | WO 93/17732 | 9/1993 |
| WO | WO 94/19036 A1 | 9/1994 |
| WO | WO 97/31666 | 9/1997 |
| WO | WO 98/07463 A1 | 2/1998 |
| WO | WO 98/10816 A1 | 3/1998 |
| WO | WO 98/11928 A1 | 3/1998 |
| WO | WO 98/12081 A1 | 3/1998 |
| WO | WO 00/16832 A1 | 3/2000 |
| WO | WO 00/38765 | 7/2000 |
| WO | WO 01/32241 A1 | 5/2001 |
| WO | WO 01/32244 A1 | 5/2001 |

OTHER PUBLICATIONS

Response filed Aug. 26, 2011 to Office Action dated May 26, 2011 regarding U.S. Appl. No. 12/836,622, 8 pgs.

* cited by examiner

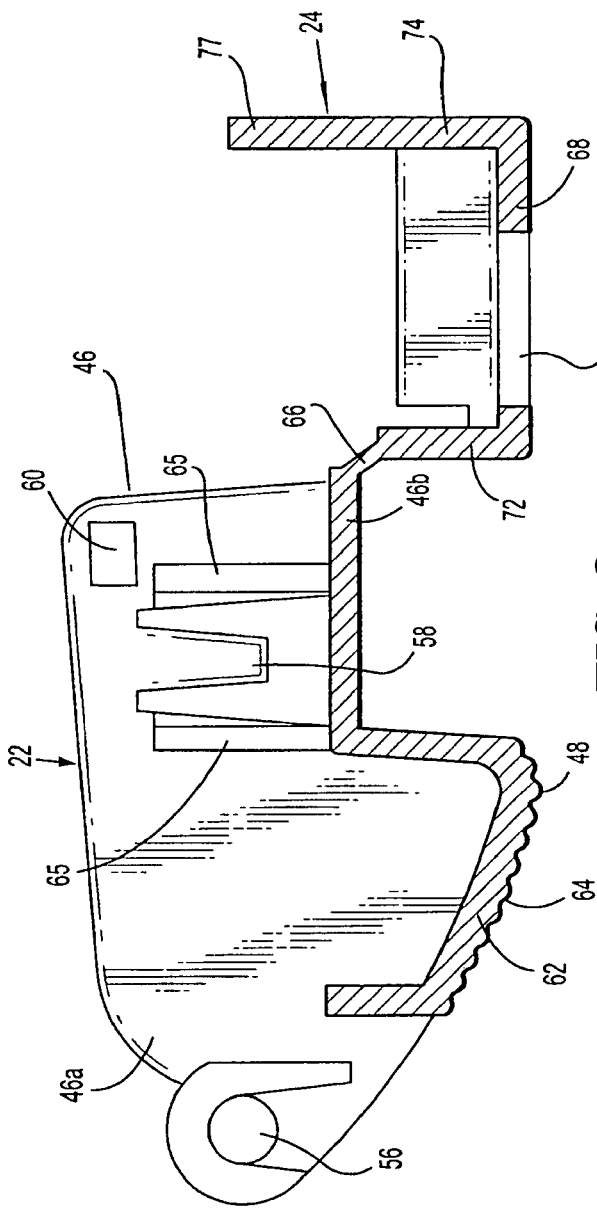
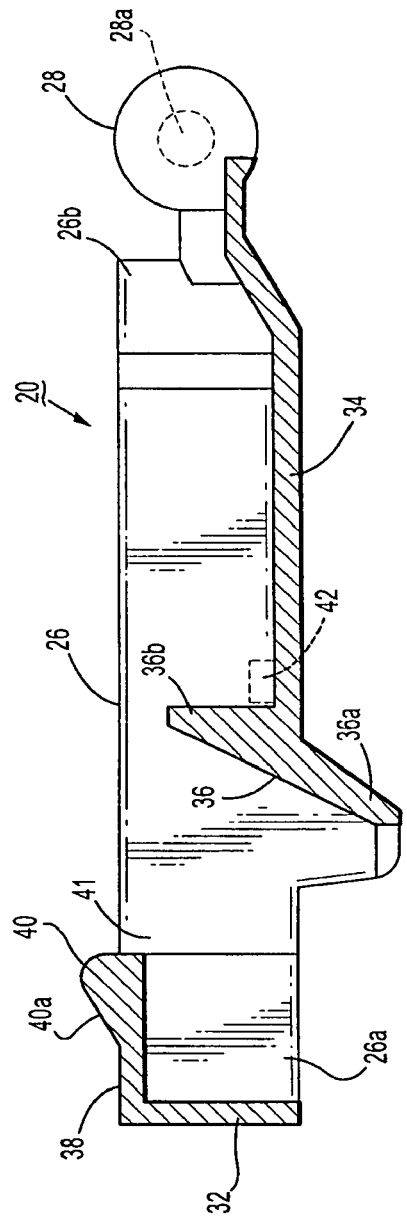
FIG. 6
FIG. 7

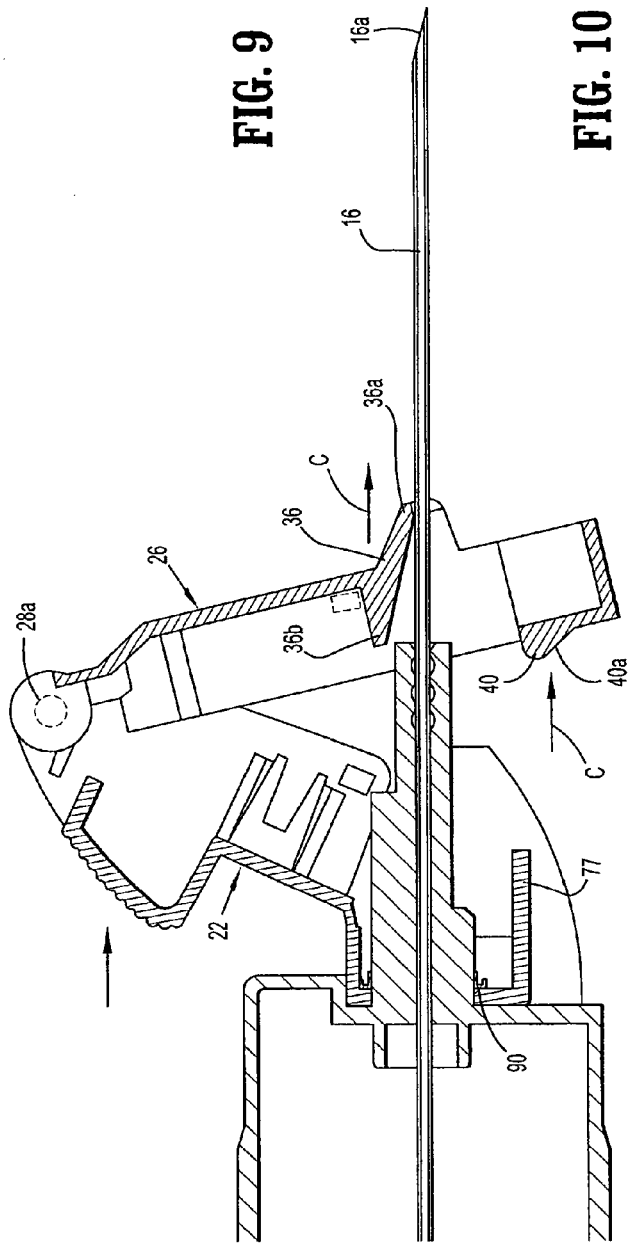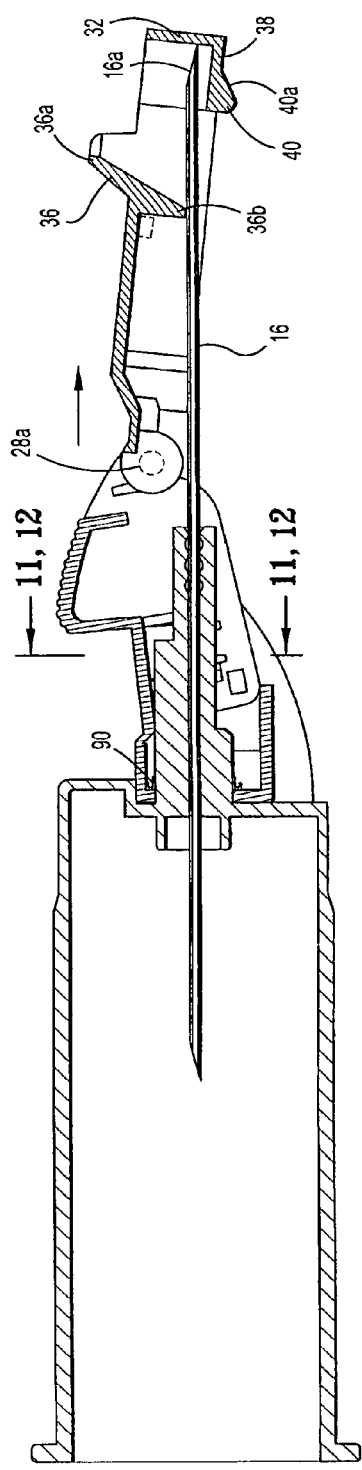

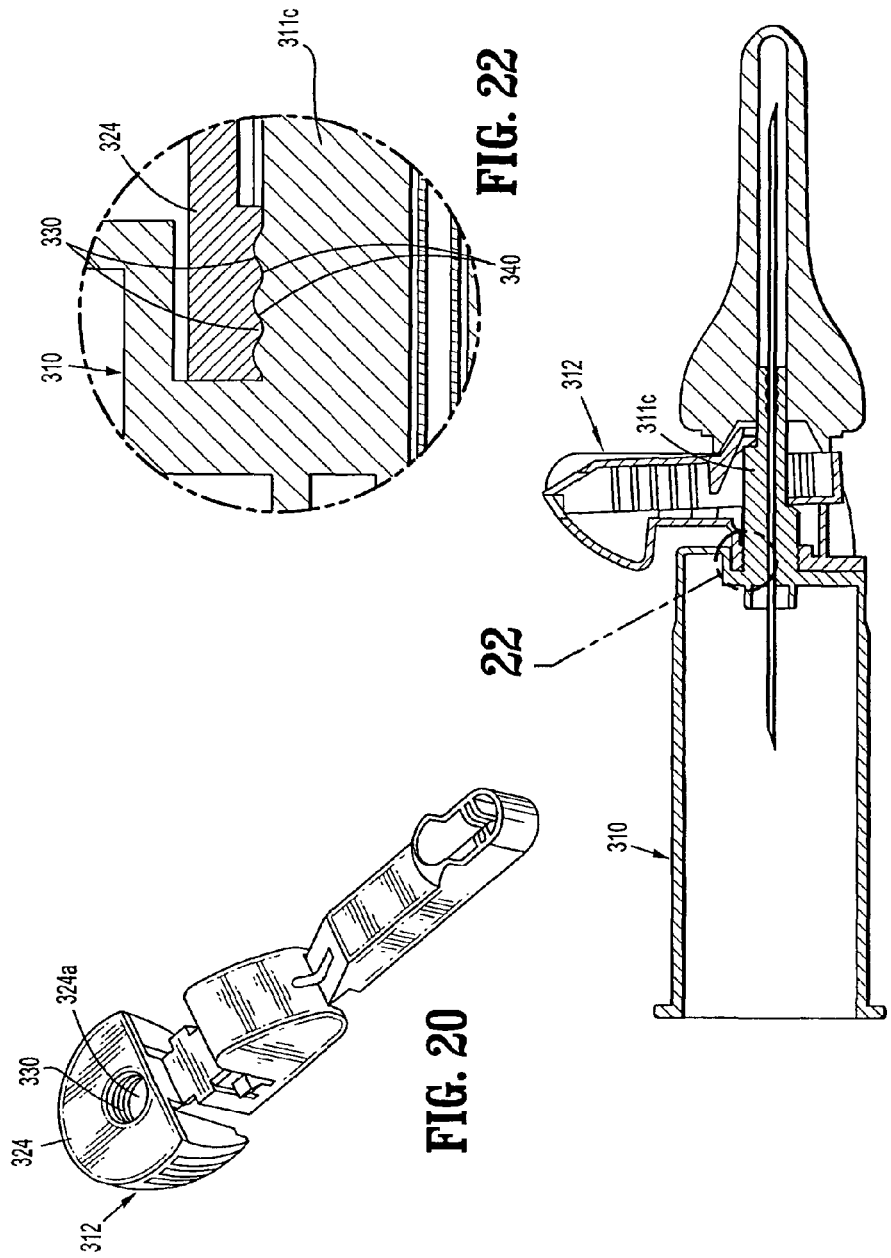

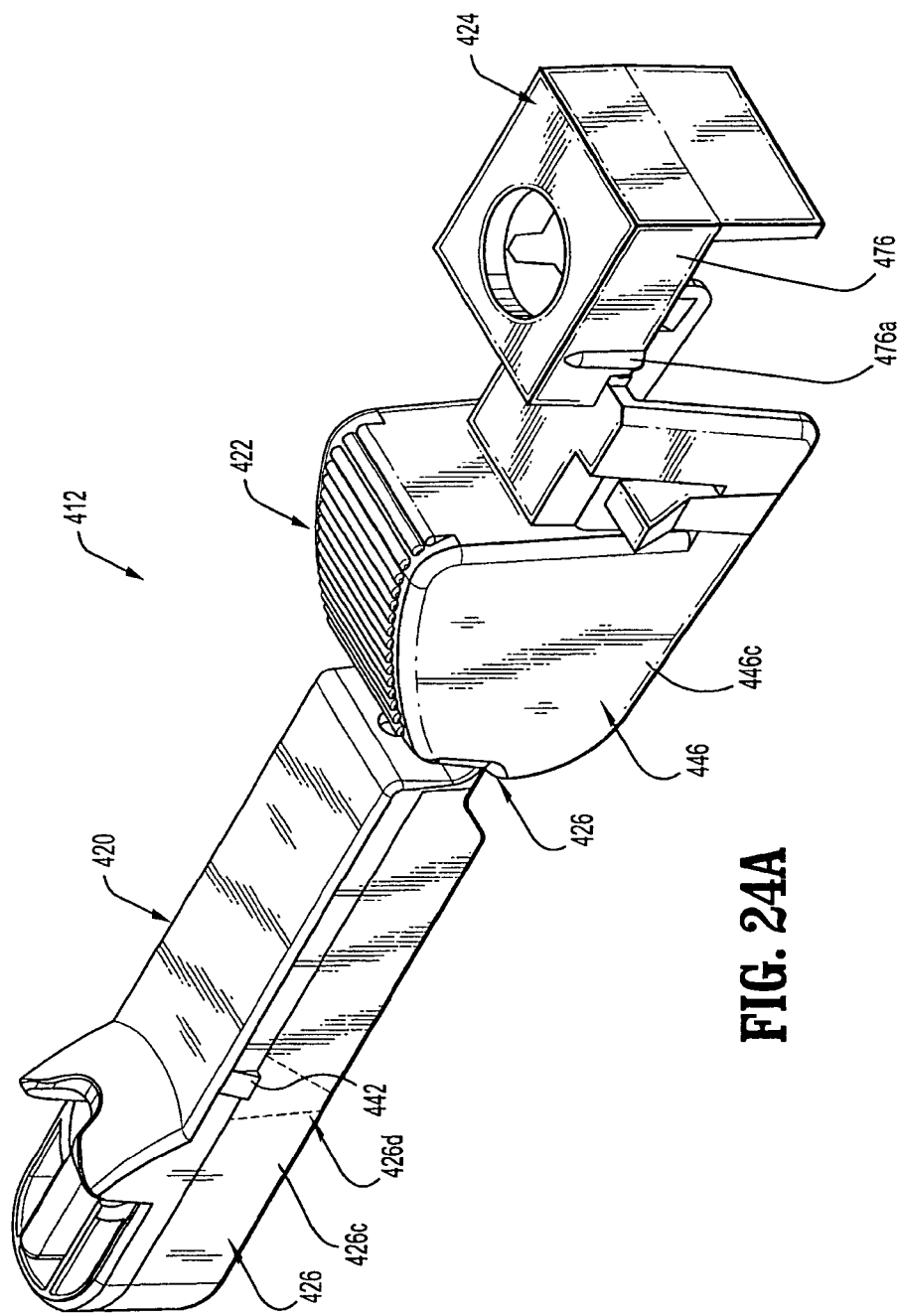

SAFETY SHIELD APPARATUS AND MOUNTING STRUCTURE FOR USE WITH MEDICAL NEEDLE DEVICES

CROSS REFERENCE TO RELATED APPLICATIONS

This patent application is a continuation-in-part of U.S. patent application Ser. No. 09/892,593, filed in the U.S. Patent and Trademark Office on Jun. 27, 2001 now U.S. Pat. No. 7,198,618, which is a continuation-in-part of U.S. patent application Ser. No. 09/433,449, filed in the U.S. Patent and Trademark Office on Nov. 4, 1999, now U.S. Pat. No. 6,280,420; application Ser. No. 09/892,593 is also a continuation-in-part of U.S. patent application Ser. No. 09/434,036, filed in the U.S. Patent and Trademark Office on Nov. 4, 1999, now U.S. Pat. No. 6,254,575; and application Ser. No. 09/892,593 is also a continuation-in-part of U.S. patent application Ser. No. 09/619,190, filed in the U.S. Patent and Trademark Office on Jul. 19, 2000, now U.S. Pat. No. 6,592,556; application Ser. No. 09/892,593 claims the benefit of U.S. Provisional Patent Application No. 60/254,506, filed in the U.S. Patent and Trademark Office on Dec. 8, 2000, and claims the benefit of U.S. Provisional Patent Application No. 60/275,810, filed in the U.S. Patent and Trademark Office on Mar. 14, 2001, now abandoned, and claims the benefit of U.S. Provisional Patent Application No. 60/275,886, filed in the U.S. Patent and Trademark Office on Mar. 14, 2001, and claims the benefit of U.S. Provisional Patent Application No. 60/296,968, filed in the U.S. Patent and Trademark Office Jun. 8, 2001. This patent application also claims the benefit of U.S. Provisional Patent Application No. 60/794,978, filed in the U.S. Patent and Trademark Office on Apr. 26, 2006. The content of each of these applications is hereby incorporated by reference herein in their entirety.

TECHNICAL FIELD

The present disclosure relates to a safety shield apparatus for use with medical needle device and, more specifically, to devices and methods for securing a safety shield apparatus to a medical needle device, e.g., a blood collection device.

BACKGROUND OF RELATED ART

Safety shields for shielding needles of medical devices are well known in the art. Safety shields minimize the risks associated inadvertent needle stick injuries which subject doctors, nurses and medical personnel to exposure to HIV, hepatitis and other serious blood-borne pathogens.

It is known to incorporate a safety shield into the body of a medical needle. More specifically, it is known to form a safety shield apparatus integrally with a medical needle device, e.g., a blood collection device. This method of securement increases the complexity of the manufacturing process. It is also known to provide a hub on the safety shield apparatus which includes a luer fitting to secure the safety shield apparatus to a medical needle device. The hub can be formed integrally with or separately from the safety shield apparatus. This method also increases the cost and complexity of the safety shield apparatus.

Accordingly, a continuing need exists in the art of safety shield apparatus for use with medical needle devices for an inexpensive, simple securement device for attaching a safety shield apparatus to a medical needle device.

SUMMARY

In accordance with the present disclosure, a safety shield apparatus is disclosed which includes a safety shield including a distal segment having a distal end and a proximal end, a proximal segment having a distal end and a proximal end, and a retention member. The proximal end of the distal segment is pivotally connected to the distal end of the proximal segment and the retention member is pivotally secured to the proximal end of the proximal segment. The retention member includes an opening dimensioned to be slidably received about a nose of a medical needle device such that the distal segment and the proximal segment of the safety shield are manually movable from a retracted position to an advanced position to shield a needle supported on the medical needle device.

In an embodiment, the safety shield apparatus includes a retention element which secures the retention member to the medical needle device.

In one embodiment, the retention element is a retention collar which is dimensioned to be frictionally engaged, e.g., press fit, about the nose of the medical needle device to secure the safety shield to the blood collection device.

In another embodiment, the opening in the retention member includes at least one annular rib dimensioned to be received within an annular recess in a nose of a medical needle device. The annular rib may be dimensioned to be received in the annular recess in an interference fit. Alternately, the opening in the retention member may include at least one annular recess dimensioned to receive an annular protrusion formed on a nose of a blood collection device. The annular recess can be dimensioned to receive the annular protrusion in an interference fit. In one embodiment, the at least one annular recess includes a series of recesses. It is also envisioned that the opening in the retention member can include a series of annular protrusions and annular recesses which are dimensioned to be received in a series of annular recesses and protrusions formed on the nose of the medical needle device.

In one embodiment, the distal segment includes a bottom or lower wall having a bearing member extending outwardly therefrom and the retention member includes a wall extension. The bearing member is positioned to rest on the wall extension when the safety shield is in its retracted position. The bearing member can include an angled top surface which engages the wall extension during initial movement of the safety shield from the retracted position to the advanced position to slidably urge the distal end of the distal segment towards its advanced position.

In another embodiment, the distal segment includes an angled extension having a distal end extending outwardly from the top wall. The angled extension is configured to engage and slide along at least one of the needle and the nose of a medical needle device. The angled extension can include a proximal end which extends from the top wall towards a plane defined by the bottom wall. The proximal end of the angled extension can be positioned to engage a needle of a medical needle device when the safety shield is in its advanced position.

In an embodiment, the proximal segment and the distal segment are pivotally connected by a pin hinge. The pin hinge may be formed by cooperating elements on the proximal and distal segments. The retention member may be integrally formed with the proximal segment.

In still another embodiment, the proximal segment and the distal segment are manufactured as a single piece having a thinned transition region which pivotally interconnects the proximal segment and distal segment to one another. The retention member may also be integrally formed with the proximal and distal segments.

It is contemplated that in one embodiment, the safety shield apparatus may be configured and adapted for use with a blood collector or a hypodermic needle.

According to another aspect of the present disclosure, a manually advanceable safety shield apparatus is disclosed which includes a safety shield having a distal segment having a distal end and a proximal end, a proximal segment having a distal end and a proximal end, and a retention member. The proximal end of the distal segment is pivotally connected to the distal end of the proximal segment and the retention member is pivotally secured to the proximal end of the proximal segment.

The retention member includes an opening dimensioned to be slidably received about a nose of a medical needle device such that the distal segment and the proximal segment of the safety shield are manually movable from a retracted position to an advanced position to shield a needle supported on the medical needle device.

The safety shield further includes a retention collar dimensioned to be frictionally engaged about the nose of the medical needle device to secure the safety shield to the medical needle device. The distal segment includes an angled extension having a distal end extending outwardly from the top wall. The angled extension is configured to engage and slide along at least one of the needle and the nose of the medical needle device during movement of the safety shield toward the advanced position.

In an embodiment, the distal segment of the safety shield includes a body portion having a top wall, a bottom wall and a bearing member extending outwardly from the bottom wall. The retention member includes a wall extension, wherein the bearing member is positioned to rest on the wall extension when the safety shield is in the retracted position.

In another embodiment, the proximal segment and the distal segment are pivotally connected by a pin hinge. The pin hinge may be formed by cooperating elements on the proximal and distal segments. The retention member may be integrally formed with the proximal segment.

In yet another embodiment, the proximal segment and the distal segment may be manufactured as a single piece having a thinned transition region which pivotally interconnects the proximal segment and distal segment to one another. The retention member may also be integrally formed with the proximal and distal segments.

BRIEF DESCRIPTION OF THE DRAWINGS

Various embodiments of the presently disclosed safety shield apparatus and mounting structure are disclosed herein with reference to the drawings, wherein:

FIG. 6 is a side cross-sectional view taken along section lines 6-6 of FIG. 5;

FIG. 7 is a side cross-sectional view taken along section lines 7-7 of FIG. 3A;

FIG. 9 is a side cross-sectional view of the blood collection device and safety shield apparatus shown in FIG. 8 with the safety shield apparatus in a more advanced position;

FIG. 10 is a side cross-sectional view of the blood collection device and safety shield apparatus shown in FIG. 9 with the safety shield apparatus in a fully advanced position;

FIG. 20 is a perspective view of yet another embodiment of the presently disclosed safety shield apparatus;

FIG. 21 is a side cross-sectional view of the safety shield apparatus shown in FIG. 20 secured to a blood collection device;

FIG. 22 is an enlarged view of the indicated area of detail shown in FIG. 21;

FIG. 24A is a top, perspective view of safety shield according to another embodiment of the present disclosure;

DETAILED DESCRIPTION OF THE EMBODIMENTS

Figure 1:
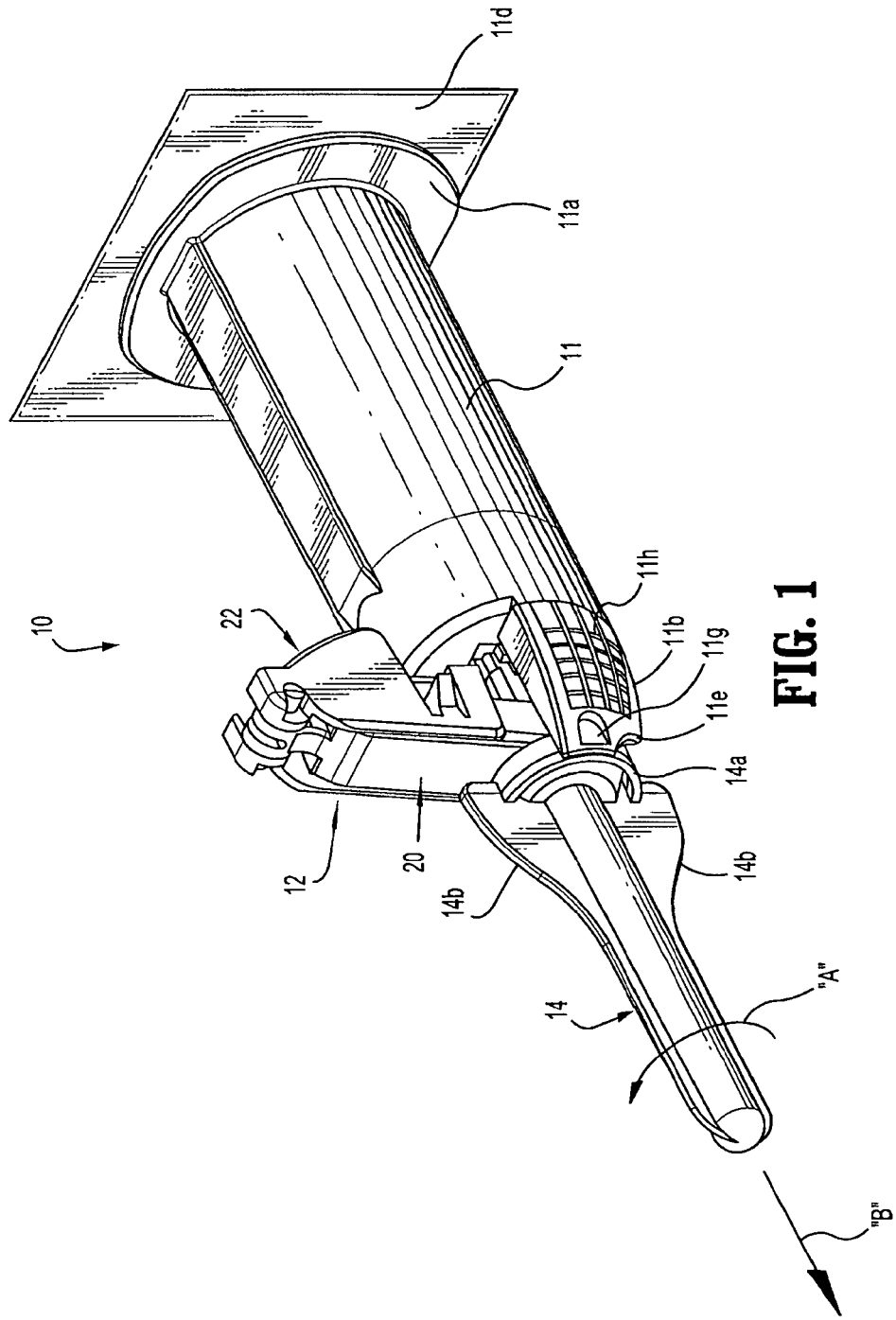
FIG. 1 is a perspective view of one embodiment of the presently disclosed safety shield apparatus secured to a blood collection device and including a sheath shielding the needle.

Embodiments of the presently disclosed safety shield apparatus and mounting structure will now be described in detail with reference to the drawings wherein like reference numerals designate identical or corresponding elements in each of the several views.

In this description, the term proximal is generally used to indicate relative nearness of a referenced item to a user of the device and the term distal is used to indicate relative remoteness of a referenced item to a user of the device.

FIG. 1 illustrates a blood collection device 10 having a safety shield apparatus 12 mounted thereon and a removable sheath 14 positioned about a needle 16 (FIG. 2) of collection device 10. Blood collection device 10 includes a blood collector barrel 11 which defines a cylindrical chamber 18 which is dimensioned to receive a blood collection vial (not shown). A proximal end of needle 16 (not shown) is positioned within cylindrical chamber 18 and is configured to pierce a stopper supported on one end of the blood collection vial.

Figure 1A:
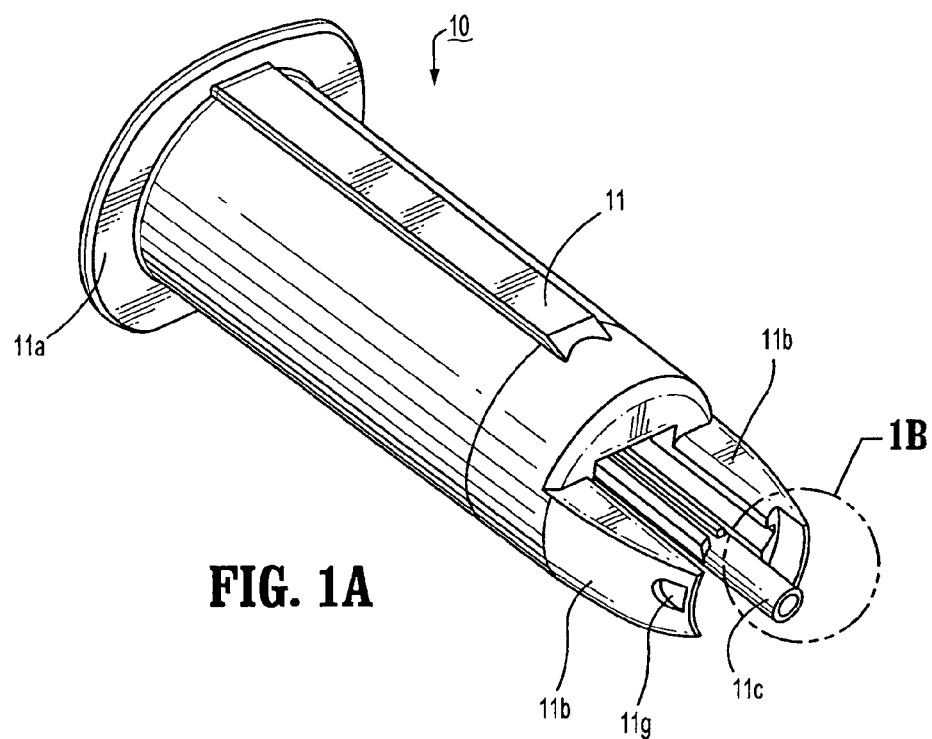
FIG. 1A is a perspective view from the distal end of a blood collection device according to another embodiment of the present disclosure.
Figure 1B:
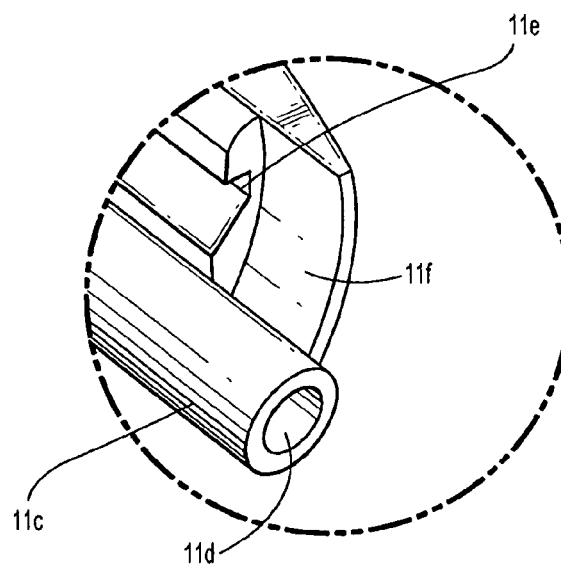
FIG. 1B is an enlarged view of the indicated area of detail shown in FIG. 1A.

As shown in FIGS. 1A and 1B, blood collector barrel 11 includes a finger flange 11a, a pair of spaced extensions or towers 11b and a nose 11c. Nose 11c defines a throughbore 11d (FIG. 1B) which is dimensioned to receive and frictionally retain needle 16 (FIG. 2) therein. In one embodiment, finger flange 11a is dimensioned or of a size to facilitate creation of a positive seal between a proximal face 13 (FIG. 1) of finger flange 11a and a peelable lid 11d (FIG. 1) secured to proximal face 13 of finger flange 11a. Peelable lid 11d can be secured to finger flange 11a using an adhesive or the like and can function to prevent dust or debris from entering cylindrical chamber 18 or as a sterile barrier which assures sterility of cylindrical chamber 18.

Spaced extensions 11b are positioned on opposite sides of nose 11c and include recesses 11e (FIG. 1B) which will be discussed in further detail below. The inner walls at the distal end of extensions 11b define surfaces 11f for frictionally engaging a proximal flange 14a of sheath 14 to secure sheath 14 about needle 16. At least one of extensions 11b includes a land/indentation/depression/recess 11g defining a location where a heated tool can be applied to heat stake flange 14a of sheath 14 to at least one of extensions 11b, thereby securing sheath 14 to barrel 11. The heat stake provides the clinician with an indication that device 10 is new or unused and that sheath 14 has not previously been removed or tampered with.

Each extension 11b may include finger gripping sections 11h (FIG. 1) defined by an area of ridges, ribs, knurling, roughness, etc. Finger gripping sections 11h provide the clinician with relatively increased gripping, manipulating and holding ability of blood collector barrel 11 and, in turn, device 10. Turning momentarily to FIGS. 1A and 1B, in an alternate embodiment, the outer surface of each extension 11b may be smooth or non-knurled.

With continued reference to FIG. 1, each extension 11b may include a camming surface, cut-out, recess or the like 11e formed in a distal-most corner thereof. Camming surface 11e functions to aid in the removal of sheath 14 from barrel 11. In particular, in use, to remove sheath 14 from barrel 11, sheath 14 is rotated with respect to barrel 11 (as indicated by arrow "A" of FIG. 1) until at least one wing or flange 14b of sheath 14 engages camming surface 11e. Continued rotation of sheath 14 relative to barrel 11, in the direction of arrow "A", results in flange(s) 14b camming against a respective camming surface 11e and the movement of sheath 14 in an axial direction away from barrel 11 (as indicated by arrow "B" of FIG. 1) thereby facilitating the separation of sheath 14 from barrel 11. During rotation of sheath 14 relative to barrel 11, the heat state between flange 14a of sheath 14 and extension 11b of barrel 11 is broken as a result of shear forces exerted thereon.

Figure 2:
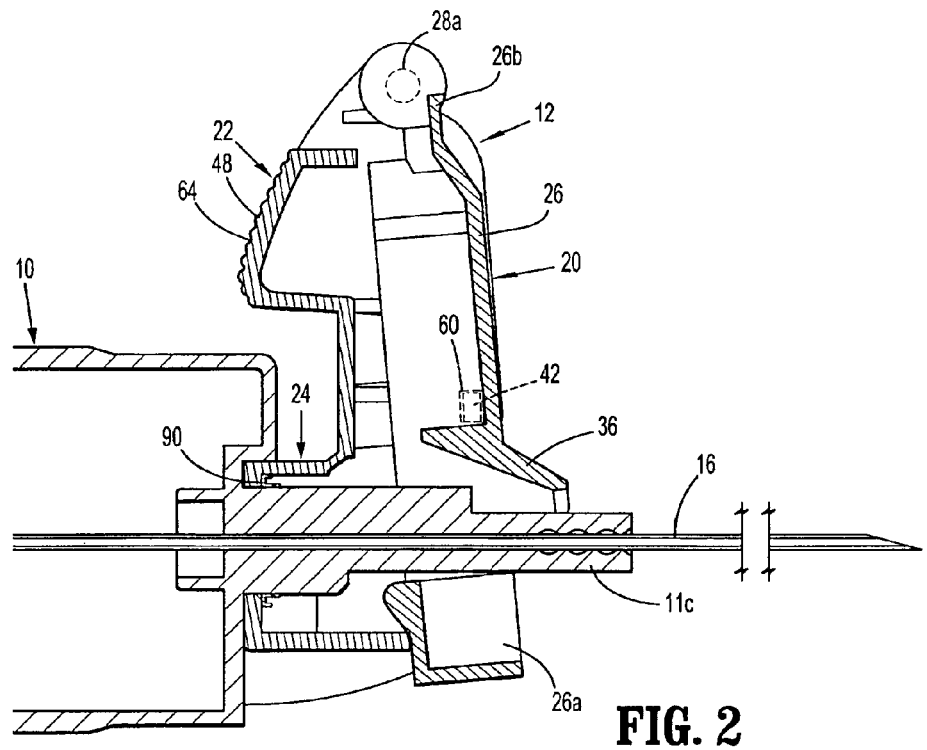
FIG. 2 is a cross-sectional view of the blood collection device and safety shield apparatus shown in FIG. 1 with the safety shield apparatus in a fully retracted position.

Referring generally to FIGS. 2-7, safety shield apparatus 12 includes a distal segment 20, a proximal segment 22 and a foot or retention member 24. Distal segment 20, which is shown in FIGS. 3A, 3B and FIG. 7, includes a body portion 26 having a distal end 26a and a proximal end 26b. A hinge member 28 is formed integrally with distal segment 20 at proximal end 26b thereof. Alternately, hinge member 28 can be formed as a separate component from distal segment 20 which is secured thereto. Further, hinge member 28 can be formed as a thinned transition region and act as a living hinge which is integrally formed between distal segment 20 and proximal segment 22. In this embodiment, hinge member 28 includes a pair of outwardly directed pivot members 28a which engage a distal end of proximal segment 22 to pivotally secure distal segment 20 to proximal segment 22 as will be discussed in further detail below. Body portion 26 defines a longitudinal channel 30 which extends through hinge member 28 along the length of body 26 to a distal wall 32 of distal segment 20. Channel 30 is dimensioned and configured to receive needle 16 (FIG. 2).

Body portion 26 has an upper wall 34 (FIG. 3B) which extends from proximal end 26b of distal segment towards distal end 26a. Upper wall 34 terminates at an angled extension or cowl 36. In one embodiment, cowl 36 includes a curved distal end 36a and a proximal end 36b (FIG. 7). While proximal end 36b of cowl 36 is shown as extending linearly with distal end 36a, it is contemplated that proximal end 36b need not extend linearly from distal end 36a but may extend at an angle with respect to distal end 36a. Alternatively, proximal end 36b of cowl 36 may be replaced by any wall (not shown) extending downwardly from an inner surface of body portion 26 at any location along a length of body portion 26. Cowl 36 is positioned to engage and slide along at least one of nose 11c and needle 16 as safety shield apparatus 12 is moved from a retracted position to an advanced position as will be discussed in further detail below.

In one embodiment, body portion 26 also includes a lower wall 38 (FIG. 3A) positioned at distal end 26a of distal segment 20. A cam or bearing member 40 which includes an angled surface 40a is formed on lower wall 38. Bearing member 40, as will be discussed in further detail below, reduces or minimizes the likelihood of stalling or binding of safety shield apparatus 12 in its retracted position. An opening or throughbore 41 is formed in distal segment 20 between cowl 36 and lower wall 38.

Body portion 26 also includes locking tabs 42 (FIG. 4) and a series of ribs 44. Locking tabs 42 are positioned on opposite sides of distal segment 20 for releasably securing safety shield apparatus 12 in its retracted position as will be discussed below. Ribs 44 provide rigidity to distal segment 20.

Figure 5:
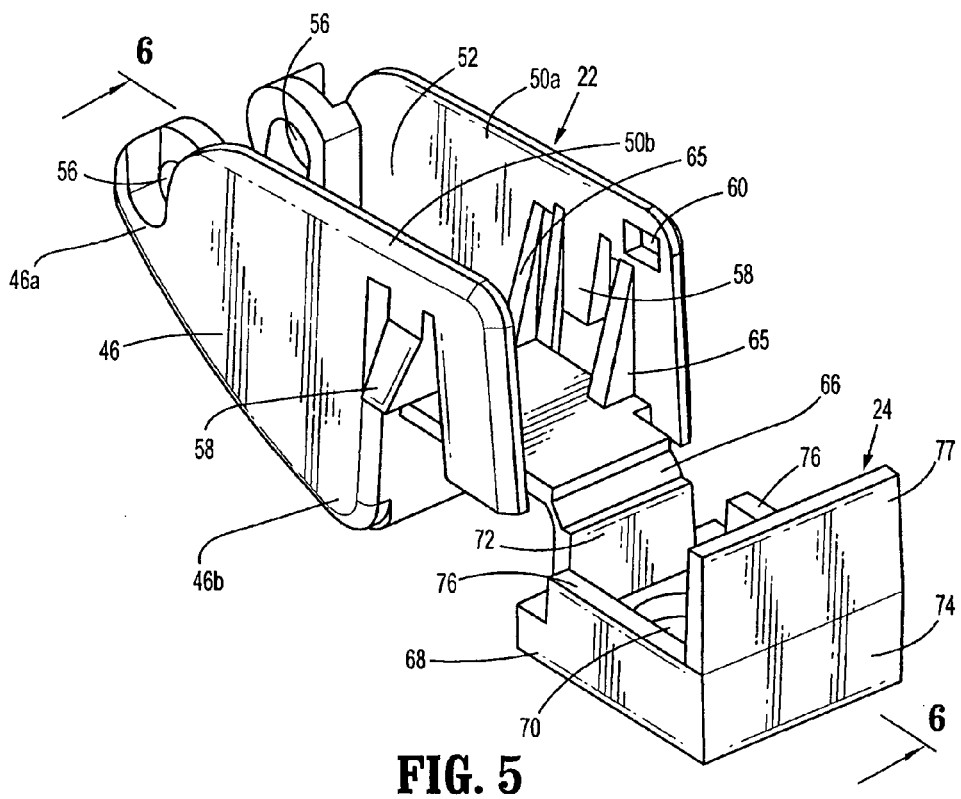
FIG. 5 is a bottom perspective view of the proximal segment and retention member of the safety shield apparatus shown in FIG. 1.

Referring also to FIGS. 5 and 6, proximal segment 22 includes a body 46 having a distal end 46a and a proximal end 46b. Body 46 includes a top surface 48 (FIG. 6) and a pair of spaced sidewalls 50a and 50b. Spaced sidewalls 50a and 50b define a channel 52 which is dimensioned to receive distal segment 20 when safety shield apparatus 12 is in its retracted position. Channel 52 also allows passage of nose 11c of blood collection device 10 and needle 16. Distal end 46a of proximal segment 22 includes an opening 56 formed in each sidewall 50a and 50b. Openings 56 are dimensioned to receive pivot members 28a of hinge member 28 (FIG. 3A) to pivotally secure distal segment 20 to proximal segment 22. As discussed above, hinge member 28 and openings 56 may be replaced with a living hinge. Each sidewall 50a and 50b of proximal segment 22 also includes a cantilevered tab 58 and a cutout 60. Cantilevered tabs 58 are positioned to be received within recesses 11e of blood collection device 10, as will be discussed in further detail below, to lock safety shield apparatus 12 in an advanced position. Each cutout 60 is positioned to receive a respective tab 42 (FIG. 3B) of distal segment 20 to releaseably secure safety shield apparatus 12 in its retracted position.

In one embodiment, top surface 48 of body 46 of proximal segment 22 includes a thumb engagement member 62 which is ribbed to provide a slip-resistant thumb engaging surface 64. Sidewalls 50a and 50b also include ribs 65 for providing rigidity to sidewalls 50a and 50b of proximal segment 22.

Retention member 24 is monolithically or integrally formed with proximal segment 22 and is hingedly connected to proximal end 46b of proximal segment 22 by a living hinge 66. Alternately, retention member 24 and proximal segment 22 may be formed separately and pivotally attached with a separate hinge member. Retention member 24 includes base portion 68 which defines a mounting hole 70 for securing safety shield apparatus 12 to blood collection device 10 as will be discussed in further detail below. Retention member 24 also includes a distal wall 72, a proximal wall 74 and a pair of sidewalls 76. Distal wall 72 is integrally connected to living hinge 66 to pivotally secure retention member 24 to proximal segment 22. Proximal wall 74 includes a cantilevered extension 77 which defines a shelf upon which top surface 40a of bearing member 40 rests when safety shield apparatus 12 is in its retracted position. Sidewalls 76 and top and bottom walls 72 and 74 define a box-like structure about base portion 68 to provide strength and rigidity to retention member 24.

Figure 5A:
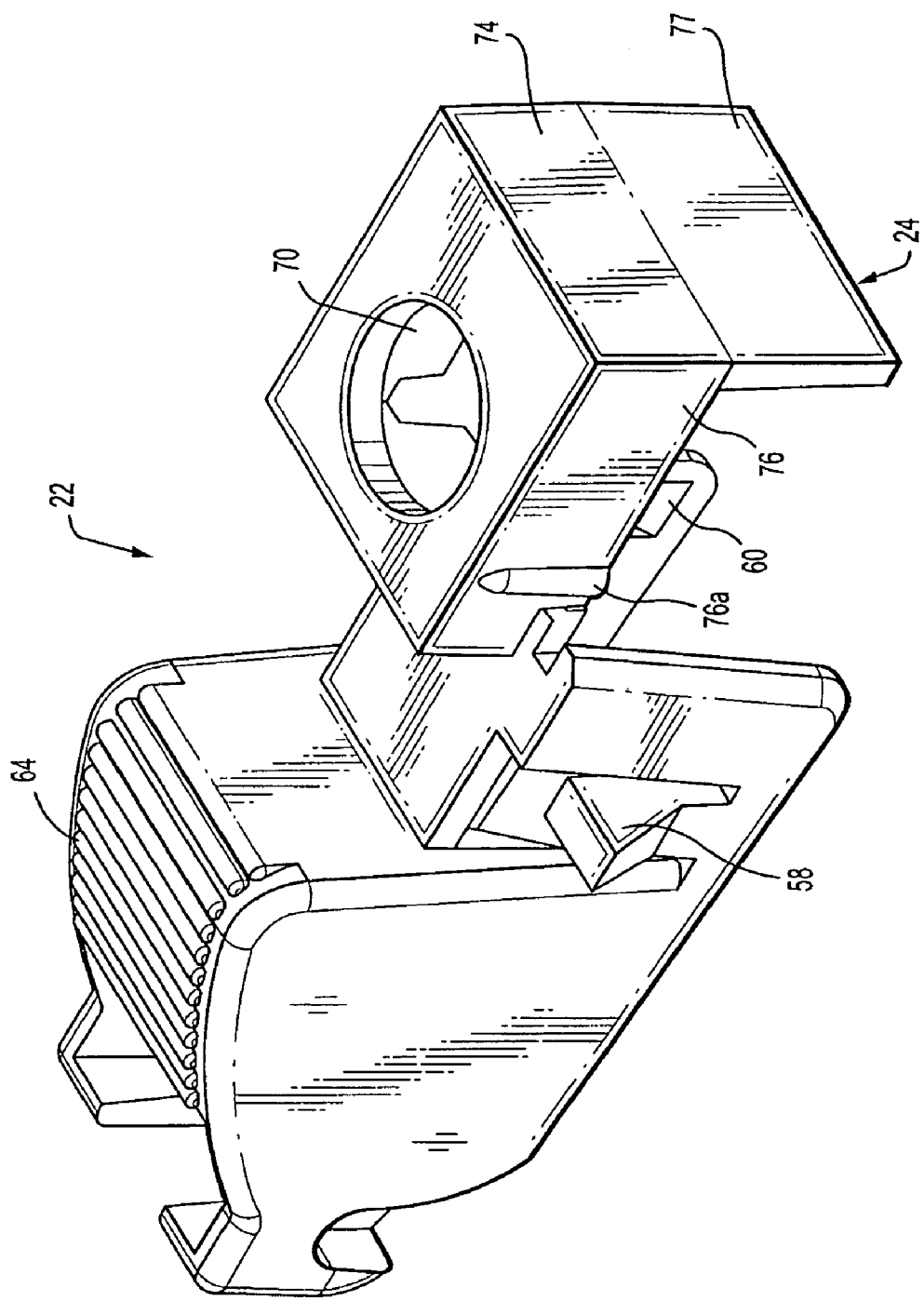
FIG. 5A is a top perspective view of a proximal segment and retention member, according to another embodiment of the present disclosure, for the safety shield apparatus shown in FIG. 1.

Referring momentarily to FIG. 5A, in an alternate embodiment, proximal section 22 may be provided with a rib 76a projecting from a surface of each side wall 76 and extending in a direction substantially parallel to a central axis of mounting hole 70. In use, when proximal section 22 is secured to blood collector barrel 11, ribs 76a slidably engage (e.g., establish an interference fit with) an inner surface of a respective extension 11b of blood collector barrel 11 (see FIGS. 1A and 1B), thereby providing increased stability therebetween.

Referring to FIG. 2, in its retracted position, safety shield apparatus 12 is supported on blood collection device 10 such that the longitudinal axes of proximal segment 22 and distal segment 20 are substantially perpendicular to a longitudinal axis of needle 16. In the retracted position of safety shield apparatus 12, tabs 42 of distal segment 20 are releasably positioned within cutouts 60 of sidewalls 50a and 50b of proximal segment 22 to releasably lock safety shield apparatus in its retracted position. Further, top surface 40a of bearing member 40 rests on cantilevered extension 77 of bottom wall 74 of retention member 24.

Figure 8:
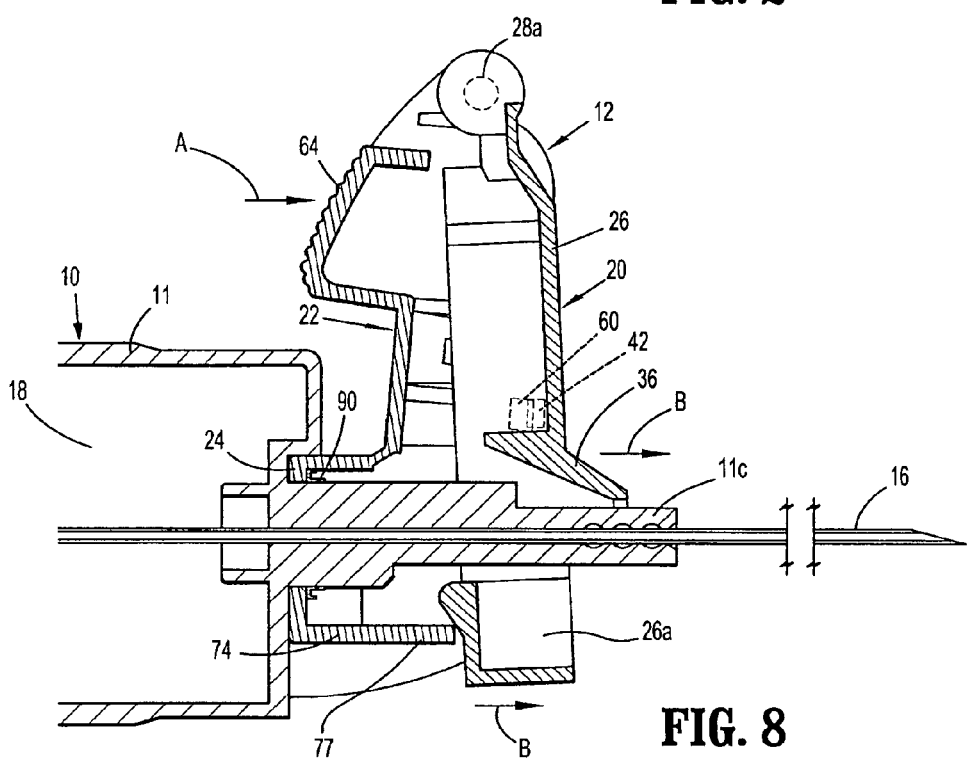
FIG. 8 is a side cross-sectional view of the blood collection device and safety shield apparatus shown in FIG. 2 with the safety shield apparatus in a partially advanced position.
Figure 3A:
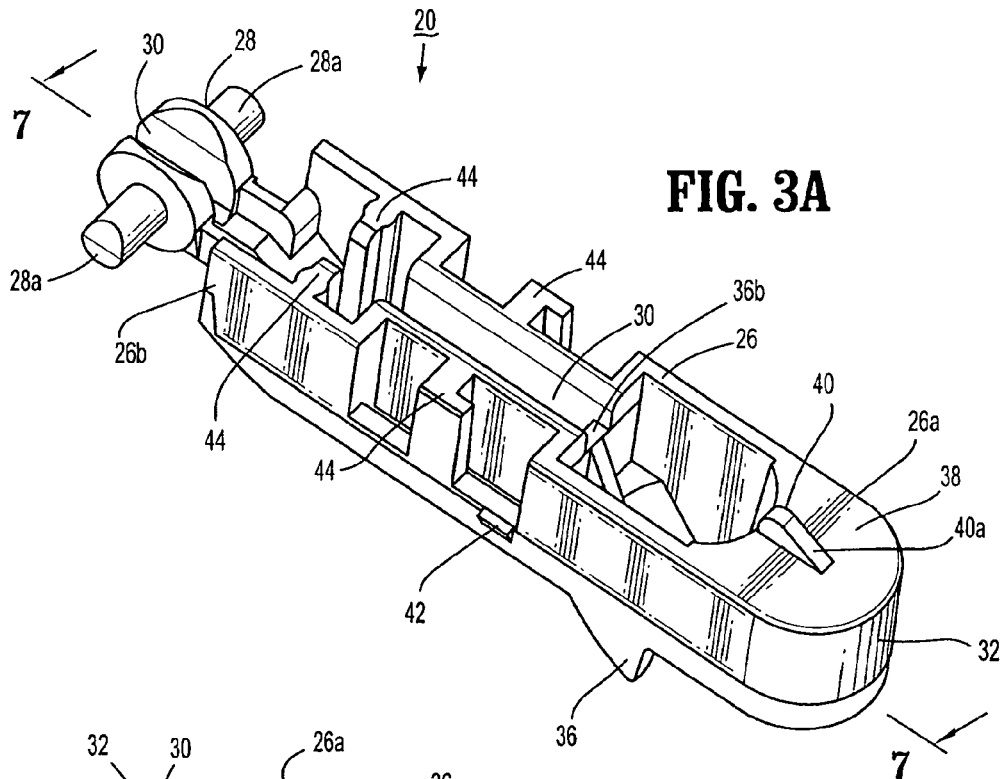
FIG. 3A is a bottom perspective view of the distal segment of the safety shield apparatus shown in FIG. 1.
Figure 3B:
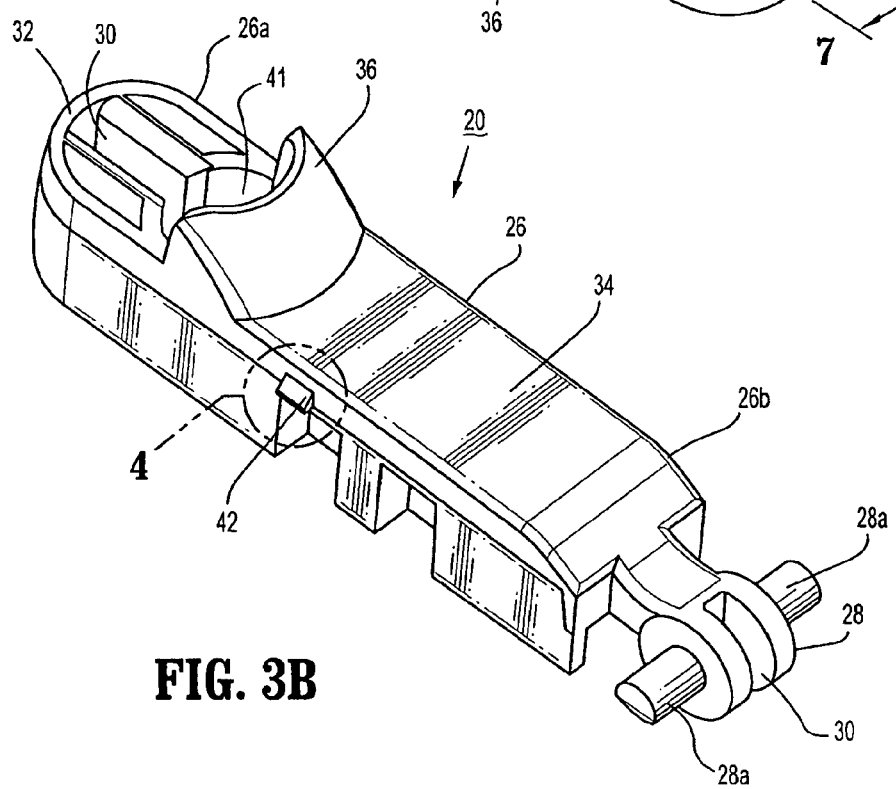
FIG. 3B is a top perspective view of the distal segment of the safety shield apparatus shown in FIG. 3A.
Figure 4:
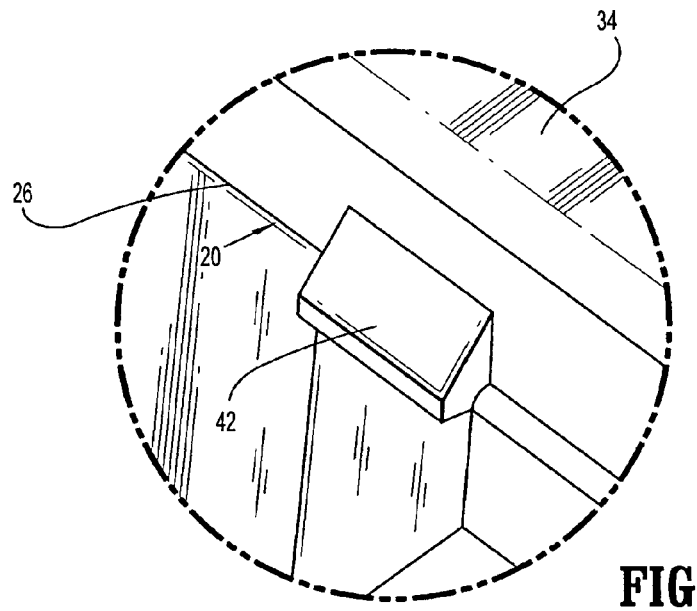
FIG. 4 is an enlarged view of the indicated area of detail shown in FIG. 3B.

Referring to FIG. 8, safety shield apparatus 12 is moved from its retracted position to its distal position by manually pressing on thumb engaging surface 64 of proximal segment 22 in the direction indicated by arrow "A". As illustrated, thumb engaging surface 64 defines an angled surface such that pressing on surface 64 creates a force having both a horizontal and a vertical component. The vertical component slidably urges top surface 40a of bearing member 40 onto extension 77 of bottom wall 74 of retention member 24. Since top surface 40a is angled as illustrated in FIG. 8, engagement between top surface 40a and extension 77 urges distal end 26a of distal segment 26 outwardly in the direction indicated by arrows "B". As this occurs, tabs 42 are forced from cutouts 60, distal end 26a moves distally along nose 11c of barrel 11 and proximal end 26b of distal segment 20 pivots in relation to distal end 46a of proximal segment 22.

In the retracted position of safety shield apparatus 12 for the embodiment shown in FIGS. 2 and 8, cowl 36 is spaced from nose 11c of blood collector barrel 11 and needle 16. Alternatively, cowl 36 rests against nose 11c after sheath 14 is removed and assists slidable urging of the distal end 26a of distal segment 26 outwardly in the direction indicated by arrows "B".

Referring to FIG. 9, as safety shield apparatus 12 is moved in the direction indicated by arrow "C" towards its advanced position, top surface 40a of bearing member 14 moves off of extension 77 and a distal edge 36a of cowl 36 of distal segment 26 moves into engagement with needle 16 to guide distal segment 26 along needle 16. As distal segment 26 is moved further distally, an inwardly extending or proximal portion of cowl 36 moves along needle 16 until only the proximal edge 36b of cowl 36 engages needle 16 when the safety shield apparatus is in its advanced position. See FIG. 10.

Figure 11:
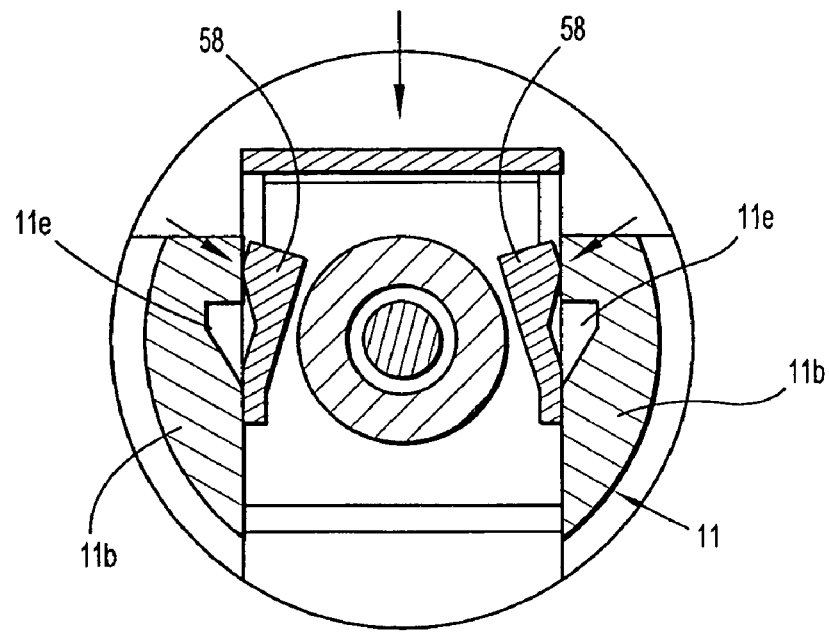
FIG. 11 is an enlarged view of the cantilevered tabs of the proximal segment of the safety shield apparatus as the cantilevered tabs are deformed by the blood collection device.
Figure 12:
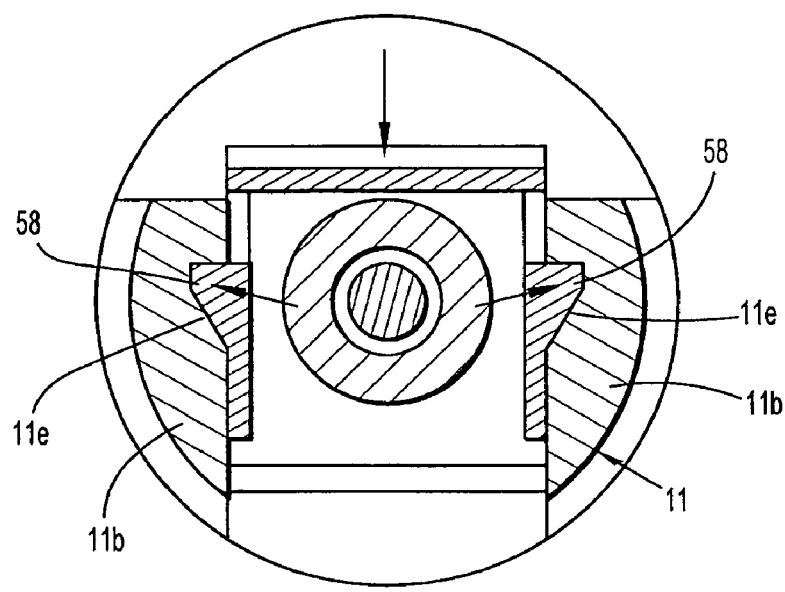
FIG. 12 is an enlarged view of the cantilevered tabs of the proximal segment of the safety shield apparatus with the cantilevered tabs positioned within recesses formed in the blood collection device.

As illustrated in FIGS. 11 and 12, as distal segment 26 is moved to its advanced position, cantilevered tabs 58 of proximal segment 22 engage an inner wall of extensions 11b of blood collector barrel 11 and are initially deflected outwardly (FIG. 11) before snapping into recesses 11e of barrel 11 (FIG. 12). Tabs 58 are positioned within recesses 11e to lock safety shield apparatus 12 in its advanced position. As illustrated in FIG. 10, in the advanced position of safety shield apparatus 12, needle 16 extends along channel 30 such that distal end 16a of needle 16 is positioned behind distal wall 32 of distal segment 26 adjacent lower wall 38.

Figure 13:
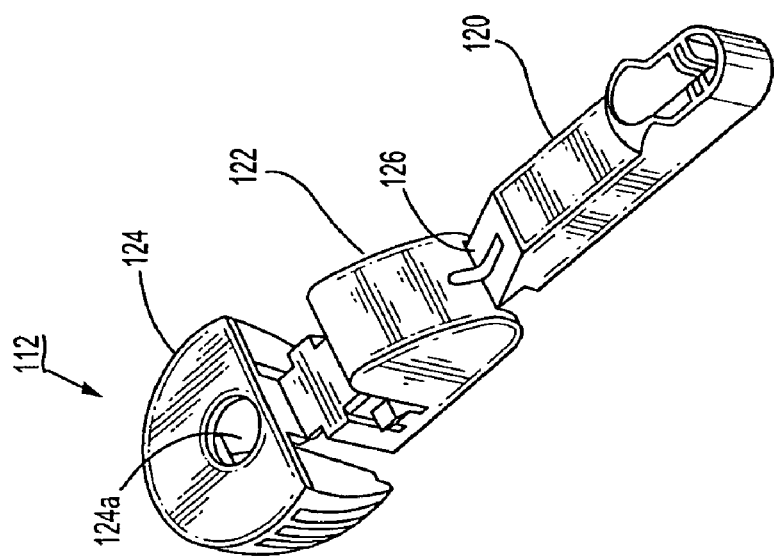
FIG. 13 is a top perspective view of an alternate embodiment of the safety shield apparatus shown in FIG. 1.

FIG. 13 illustrates an alternate embodiment of the presently disclosed safety shield apparatus shown generally as 112. Safety shield apparatus 112 is similar to safety shield apparatus 12 and includes a distal segment 120, a proximal segment 122 and a retention member 124. Proximal segment 122 is pivotally secured to distal segment 120 by a thinned transition region or living hinge 126. Safety shield apparatus 112 functions in a manner substantially similar to safety shield apparatus 12 discussed above. Thus, the operation of safety shield apparatus 112 will not be discussed in detail herein.

Figure 14:
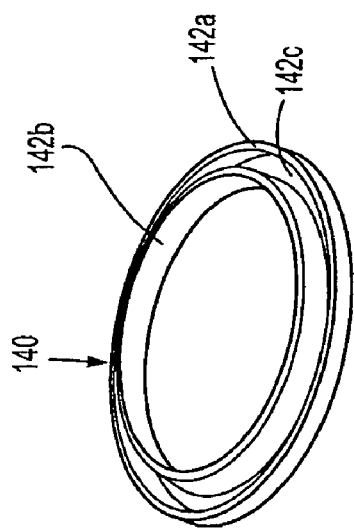
FIG. 14 is a perspective view of a locking ring for securing the safety shield apparatus to a blood collection device.
Figure 16:
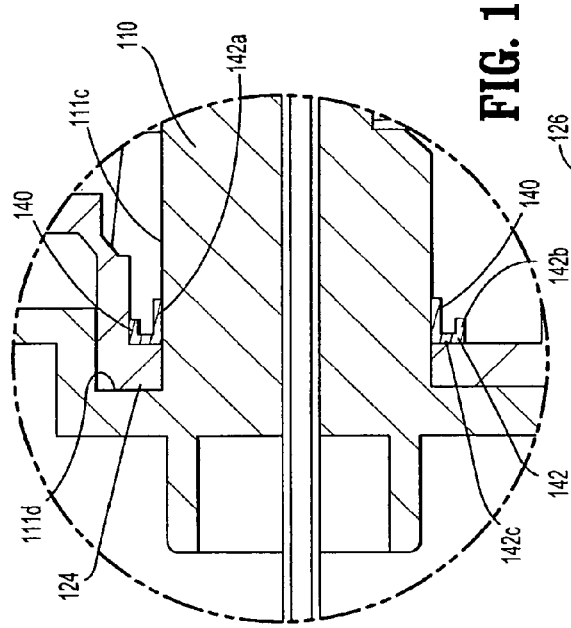
FIG. 16 is an enlarged view of the indicated area of detail shown in FIG. 15.
Figure 15:
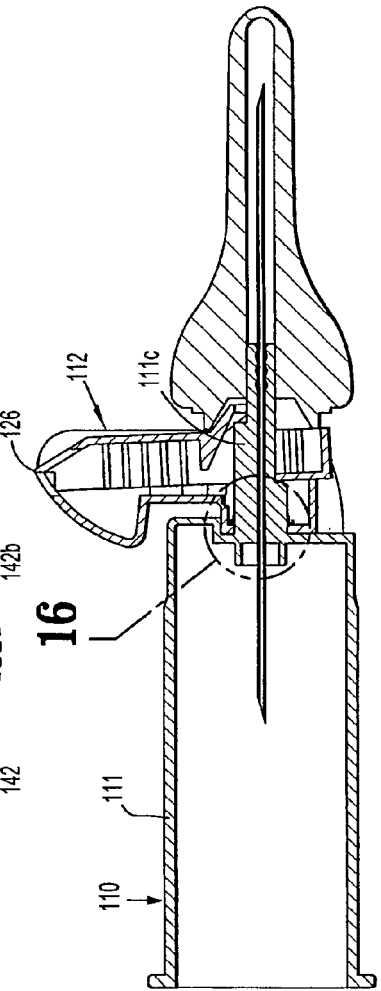
FIG. 15 is a side cross-sectional view of the safety shield apparatus shown in FIG. 13 secured to a blood collection device with the locking ring shown in FIG. 14.

FIG. 14 illustrates a retaining collar 140 for mounting safety shield apparatus 112 to a blood collection device 110 (See FIGS. 15 and 16). More specifically, retaining collar 140 includes an annular body 142 having an inner annular portion 142a and an outer annular portion 142b joined together by a backspan 142c. Inner annular portion 142a defines a diameter dimensioned to be received about a proximal portion of nose 111c of blood collection device 110.

In order to mount safety shield apparatus 112 onto blood collection device 110, retention member 124, which defines an opening 124a (FIG. 13), is positioned about nose 111c of blood collection device 110 as illustrated in FIGS. 15 and 16. Next, retaining collar 140 is pressed down over and along nose 111c to capture retention member 124 between retaining collar 140 and a distal face 111d of blood collection device 110. The tight interference fit between the inside diameter of retaining collar 140 and the outside diameter of nose 111c provides secure attachment of safety shield apparatus 112 to blood collection device 110. It is noted that safety shield apparatus 12 shown in FIGS. 1-12 is mounted on blood collector device 10 using a retaining collar 90. See FIGS. 8-10. Retaining collar 90 is substantially identical to retaining collar 140.

Figure 17:
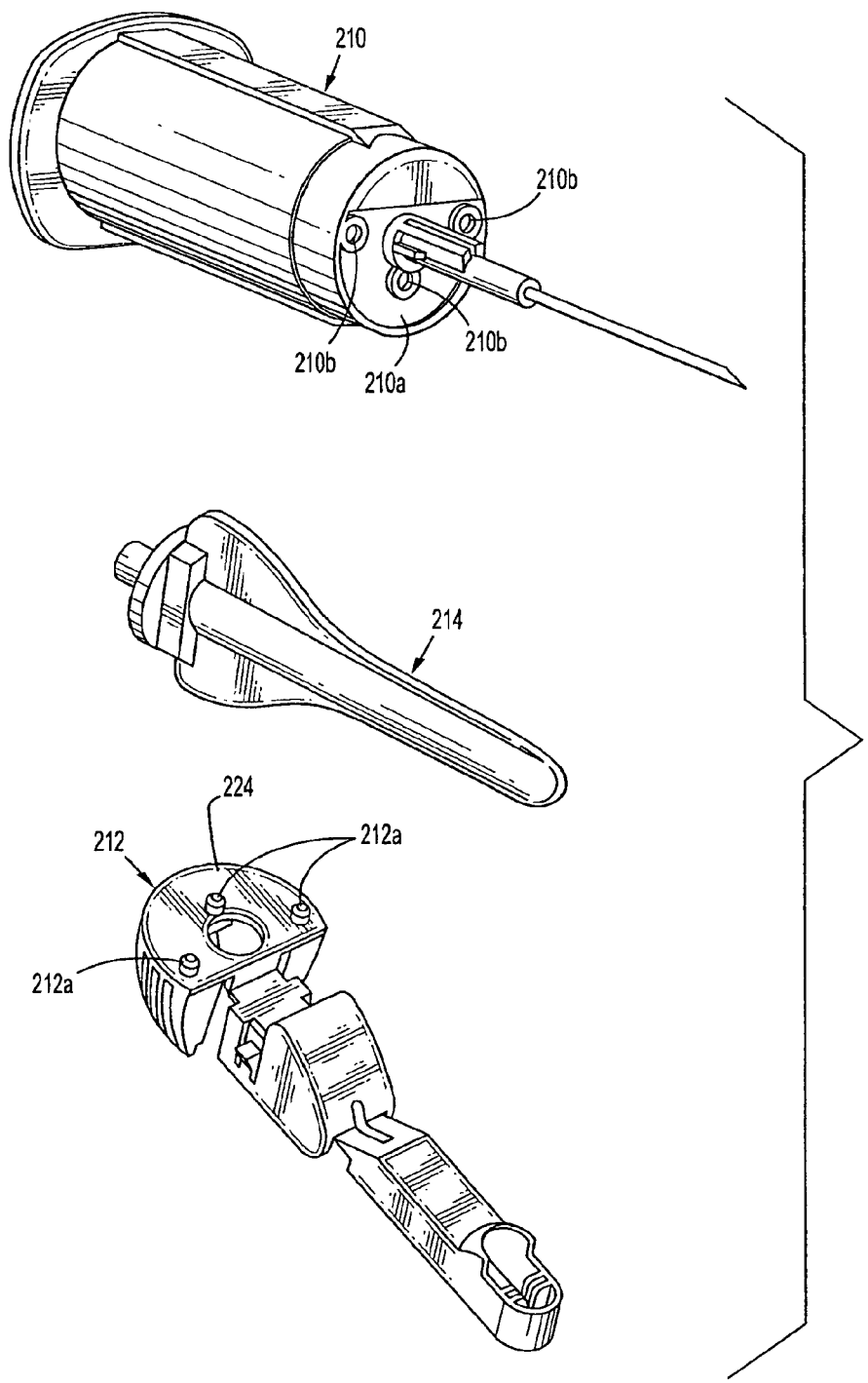
FIG. 17 is a perspective view of another embodiment of the presently disclosed safety shield apparatus, a blood collection device and sheath, shown with parts separated.
Figure 19:
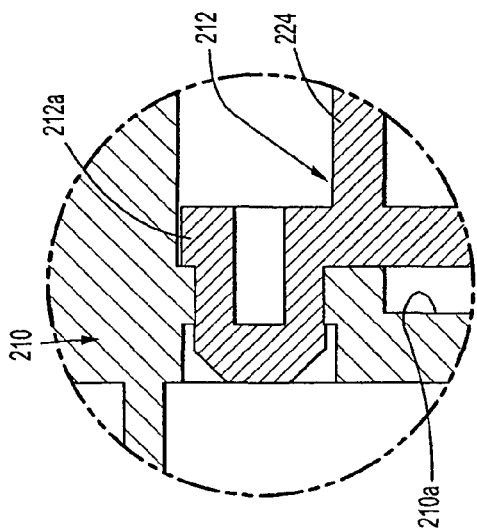
FIG. 19 is an enlarged view of the indicated area of detail shown in FIG. 18.
Figure 18:
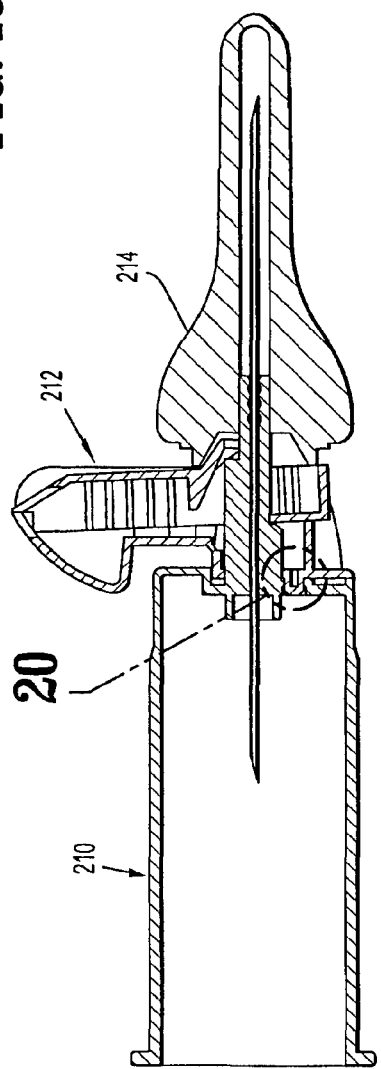
FIG. 18 is a side cross-sectional view of the safety shield apparatus, blood collection device and sheath shown in FIG. 17 assembled.

FIGS. 17-19 illustrate an alternate method and structure for securing a safety shield apparatus 212 to a blood collection device 210. More specifically, blood collection device 210 includes a distal face 210a which includes a plurality of openings 210b. Retention member 224 of safety shield apparatus 212 includes a plurality of projections 212a. In one embodiment, projections 212a include a tapered tip and are dimensioned to be press fit into openings 210b to secure safety shield apparatus 212 to blood collector device 210. Although three openings 210b and three projections 212a are illustrated, it is envisioned that one or more openings and projections may be provided, e.g., one, two, four, etc. It is also envisioned that the openings may be formed in the retention member and the projections may be formed on the blood collection device. As illustrated in FIGS. 17 and 18, the assembled device may include a protective sheath 214.

FIGS. 20-22 illustrate yet another method and structure for securing a safety shield apparatus 312 to a blood collection device 310. In this embodiment, retention member 324 of safety shield apparatus 312 includes an opening 324a which defines one or a series of annular recesses and/or ribs or protrusions 330. Nose 311c of blood collector device 310 also includes one or a series of annular recesses and/or ribs 340 which are positioned to mate with annular recesses and/or ribs 330. In this embodiment, opening 324a defines a series of recesses and ribs 330 and nose 311c includes a series of recesses and ribs 340. In order to mount safety shield apparatus 312 to blood collection device 310, retention member 324 is press fit over nose 311c of blood collector device 310 to position recesses and ribs 330 in mating alignment with annular recesses and ribs 340. The interference fit between the annular ribs and annular recesses provides secure attachment of blood collection device 310 and safety shield apparatus 312. It is noted that although ribs and recesses are illustrated as being smoothly curved other configurations are envisioned, e.g., rectangular protrusions and recesses. Further, only recesses may be provided on retention member 324 and protrusions or ribs on nose 311c of blood collection device 310, or vice versa. Moreover, the recesses and ribs need not be engaged in an interference fit, but rather they may be joined in an interlocking fashion.

Figure 23:
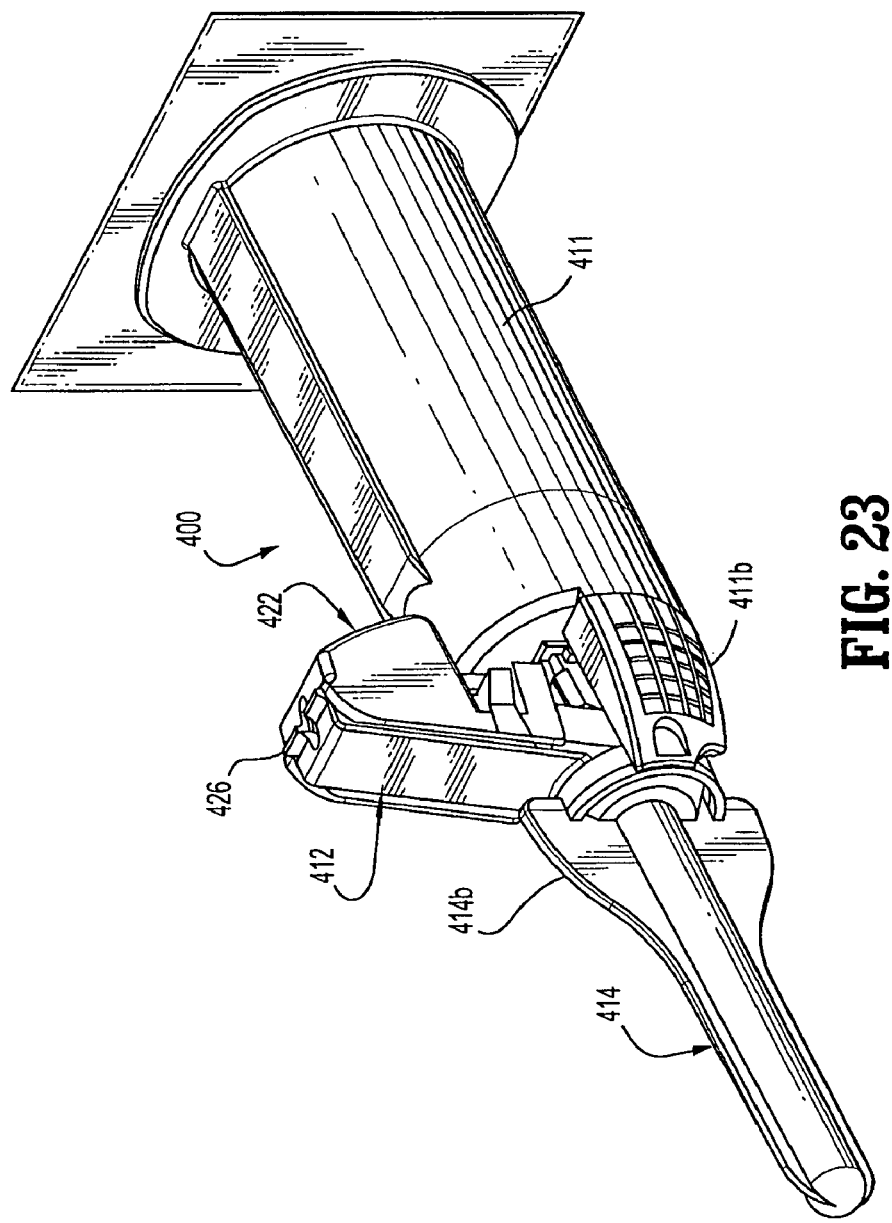
FIG. 23 is a perspective view of yet another embodiment of a safety shield apparatus secured to a blood collection device and including a sheath shielding a needle thereof.
Figure 24F:
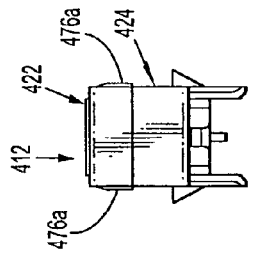
FIG. 24F is a rear, elevational view of the safety shield of FIGS. 24A-E.
Figure 24B:
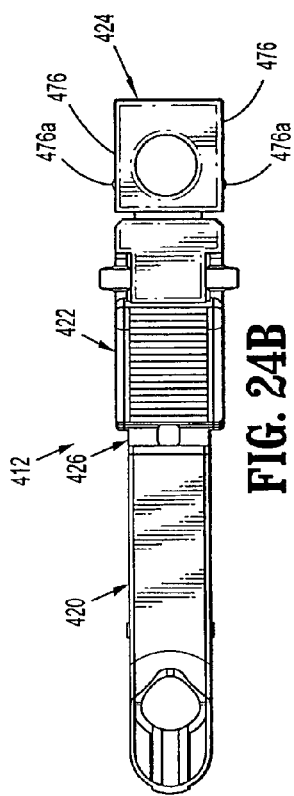
FIG. 24B is a top, plan view of the safety shield of FIG. 24A.

FIGS. 23-24F illustrate a blood collection device 400 having a safety shield apparatus 412 mounted thereon and a removable sheath 414 positioned about a needle (not shown). Safety shield apparatus 412 of blood collection device 400 is substantially similar to safety shield apparatus 112 of blood collection device 110 and thus will only be discussed in detail herein to the extent necessary to identify differences in construction and/or operation thereof.

As seen in FIGS. 23-24F, safety shield apparatus 412 includes a proximal segment 422 pivotally secured to a distal segment 420 by a thinned transition region or living hinge 426. Safety shield apparatus 412 functions in a manner substantially similar to safety shield apparatus 12 and 112 discussed above.

Figure 24C:
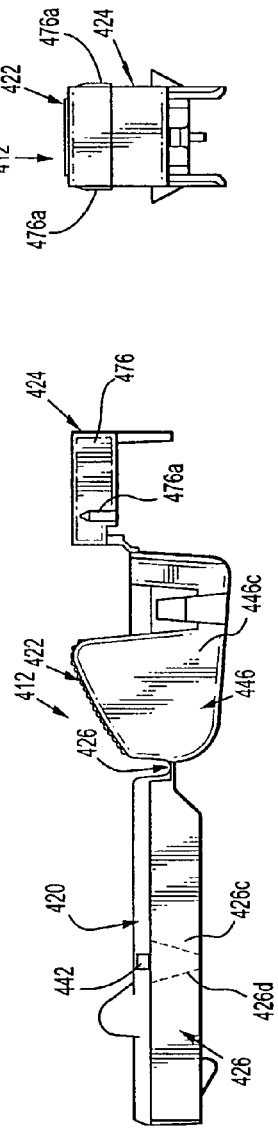
FIG. 24C is a side, elevational view of the safety shield of FIGS. 24A-B.

As best seen in FIGS. 24A and 24C, distal segment 420 includes a raised pad or the like 426d projecting from an outer surface of each side wall 426d of body portion 426. Raised pads 426d may be disposed beneath or are in registration with locking tabs 442 of body portion 426. Raised pads 426d may have a substantially triangular profile wherein a wider and/or thicker portion thereof is located closer to the respective locking tab 442. Raised pads 426d function to create a frictional engagement with a respective inner surface of a side wall 446c of body 446 of proximal segment 422, when safety shield apparatus 412 is in a retracted position, as shown in FIG. 23. The degree of friction or interference between raised pads 426d against the inner surfaces of side walls 446c of body 446 of proximal segment 422 is adjusted based on the dimensions of raised pads 426d (e.g., height, width or thickness) and the distance between side walls 446c of body 446.

Figure 24D:
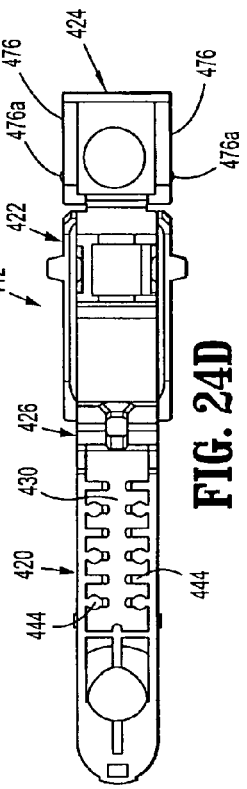
FIG. 24D is a bottom, plan view of the safety shield of FIGS. 24A-C.
Figure 24E:
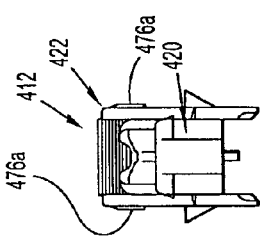
FIG. 24E is a front, elevational view of the safety shield of FIGS. 24A-D.

As seen in FIG. 24D, distal segment 420 of safety shield apparatus 412 includes a series of ribs 444 disposed on either side of an inner surface thereof and, in turn, define longitudinal channel 430. Longitudinal channel 430 extends through hinge member 426 along the length of proximal segment 422. Channel 430 is dimensioned and configured to receive needle 16 therein (FIG. 2).

As seen in FIGS. 24A-24F, proximal segment 424 of safety shield apparatus 412 includes a rib 476a projecting from a surface of each side wall 476 thereof. In use, when proximal section 422 is secured to blood collector barrel 411, ribs 476a are slidably engage (e.g., interference fit) an inner surface of a respective extension 411b of blood collector barrel 411, thereby providing increased stability therebetween.

Figure 25:
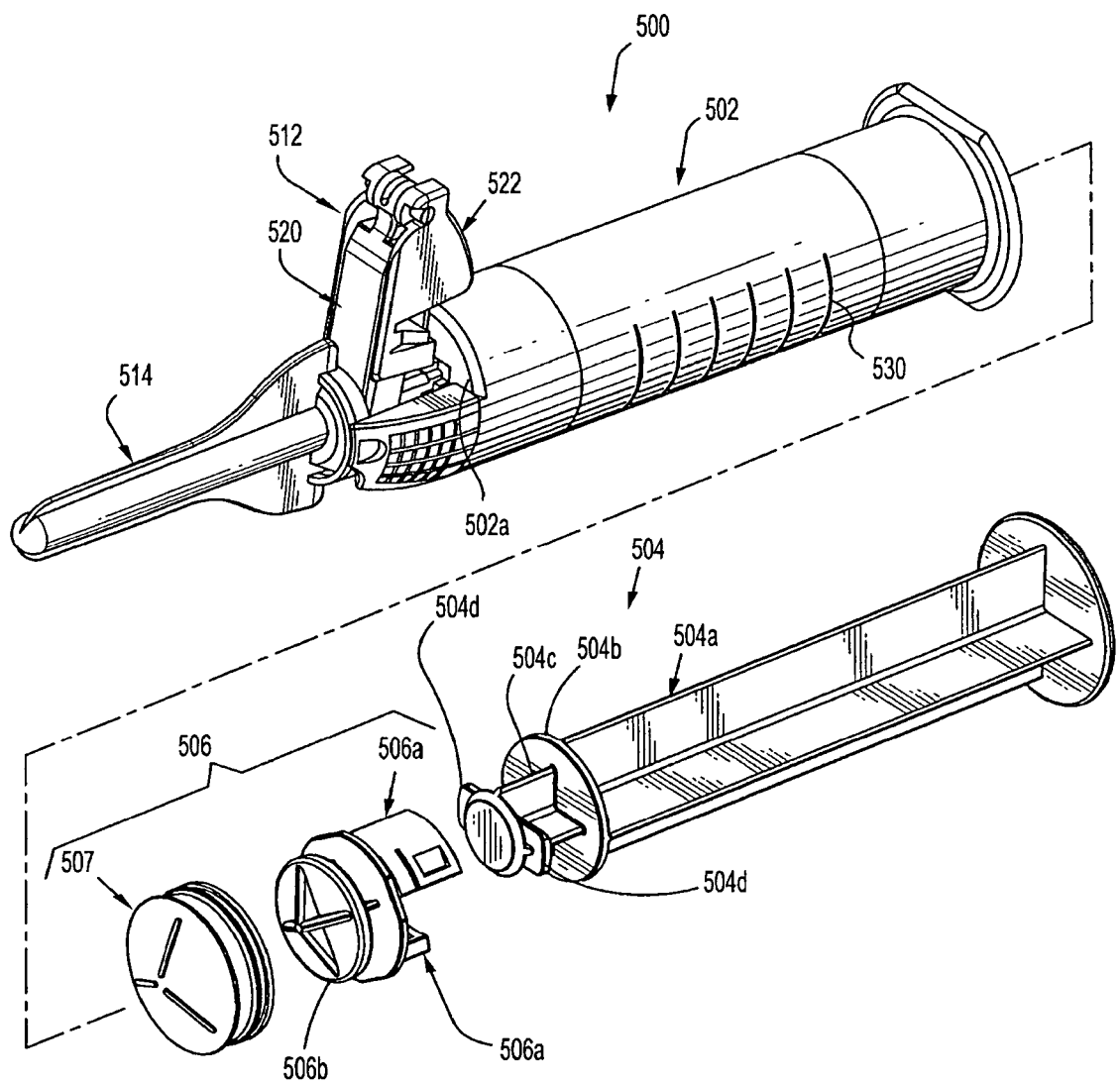
FIG. 25 is an exploded, perspective view of a hypodermic needle syringe including a safety shield according to an embodiment of the present disclosure.

Turning now to FIG. 25, a hypodermic needle syringe including a safety shield apparatus, according to an embodiment of the disclosure, is generally designated 500. Syringe 500 includes a syringe barrel 502, a plunger rod 504 slidably disposable within syringe barrel 502, and a plug 506 selectively supportable on a distal end of plunger rod 504.

As seen in FIG. 25, syringe barrel 502 is configured and adapted to support a safety shield apparatus 510 on a distal end 502a thereof. Safety shield apparatus 510 may be constructed and may operate in accordance with any of the safety shield apparatus' disclosed herein above. Distal end 502a of syringe barrel 502 is also configured and adapted to support a sheath 514 which removably covers a hypodermic needle cannula (not visible). Syringe barrel 502 preferably includes graduation marks 530 in milliliters.

Syringe 500 further includes a plunger rod 504 having an elongate plunger shaft 504a configured and dimensioned for slidable disposition within a cavity of syringe barrel 502. A distal end 504b of plunger shaft 504a may be configured and dimensioned to support plug 506 thereon. Distal end 504b may include a hub 504c extending distally therefrom and a pair of tabs 504d extending radially outwardly from hub 504c.

In one embodiment, plug 506 includes a base wall a pair of spaced apart uprights 506a extending from a first surface thereof and defining a space therebetween for selectively receiving and engaging tabs 504d of plunger rod 504. Plug 506 may include a support element 506b extending from a second surface thereof, opposite the first surface. Plug 506 further includes a resilient plunger tip 507 supported on support element 506b thereof. Plunger tip 507 includes a proximal surface (not shown) configured and adapted to selectively engage with support element 506b of plug 506 in a snap-over-type engagement.

Safety shield apparatus 512 functions in a manner substantially similar to safety shield apparatus 12 and 112 discussed above and thus will not be discussed in further detail herein.

It will be understood that various modifications may be made to the embodiments disclosed herein. Although the above description is described in association with a blood collection device, it is envisioned that the presently disclosed safety apparatus and mounting structure may be used with other medical needle devices, e.g., syringes, hypodermic needles, wing-set needles, blood draw needles, etc. Therefore, the above description should not be construed as limiting, but merely as exemplifications of preferred embodiments. Those skilled in the art will envision other modifications within the scope and spirit of the claims appended hereto.

What is claimed is:

1. A safety shield apparatus comprising:
a safety shield including a distal segment having a distal end and a proximal end, a proximal segment having a distal end and a proximal end, and a retention member, the proximal end of the distal segment being pivotally connected to the distal end of the proximal segment and the retention member being pivotally secured to the proximal end of the proximal segment, the retention member being dimensioned to be frictionally engaged directly about a nose of a medical needle device to secure the safety shield to the medical needle device, wherein when the safety shield is in a fully retracted position a tip of the nose of the medical needle device extends distally through and beyond the distal segment of the safety shield in such a manner that a cowl at a tip of the distal segment of the safety shield is positioned over the nose of the medical needle device without contacting the needle;
wherein the retention member includes an opening dimensioned to be non-rotationally and slidably received about a nose of a medical needle device such that the distal segment and the proximal segment of the safety shield are manually movable in a slidable manner across a surface of a the needle, from the fully retracted position to an advanced position, to shield the needle supported on the medical needle device; and
a retention collar having a configuration for securing the retention member directly to the nose of the medical needle device via an interference fit.

2. The safety shield apparatus according to claim 1, wherein the retention collar includes an inner annular portion defining a diameter that is less than a diameter of the nose of the medical needle device.

3. The safety shield apparatus according to claim 1, wherein the opening in the retention member includes at least one annular rib dimensioned to be received within an annular recess in a nose of a medical device.

4. The safety shield apparatus according to claim 3, wherein the annular rib is dimensioned to be received in the annular recess in an interference fit.

5. The safety shield apparatus according to claim 1, wherein the opening in the retention member includes at least one annular recess dimensioned to receive at least one annular protrusion formed on the nose of the medical needle device.

6. The safety shield apparatus according to claim 5, wherein the at least one annular recess is dimensioned to receive the annular protrusion in an interference fit.

7. The safety shield apparatus according to claim 5, wherein the at least one annular recess includes a series of recesses.

8. The safety shield apparatus according to claim 7, wherein the opening in the retention member also includes a series of annular protrusions which are dimensioned to be received in a series of annular recesses formed on the nose of the medical needle device.

9. The safety shield apparatus according to claim 1, wherein the distal segment of the safety shield includes a body portion having a top wall, a bottom wall and a bearing member extending outwardly from the bottom wall, the retention member including a wall extension, wherein the bearing member is positioned to rest on the wall extension when the safety shield is in the retracted position.

10. The safety shield apparatus according to claim 9, wherein the bearing member includes an angled top surface, the angled top surface engaging the wall extension during initial movement of the safety shield from the retracted position to the advanced position to slidably urge the distal end of the distal segment towards the advanced position.

11. The safety shield apparatus according to claim 1, wherein the distal segment includes an angled extension having a distal end extending outwardly from a top wall, the angled extension being configured to engage and slide along at least one of the needle and the nose of the medical needle device during movement of the safety shield toward the advanced position.

12. The safety shield apparatus according to claim 11, wherein the angled extension includes a proximal end which extends from the top wall towards a plane defined by the bottom wall, the proximal end of the angled extension being positioned to engage a needle of a medical needle device when the safety shield is in the advanced position.

13. The safety shield apparatus according to claim 1, wherein the proximal segment and the distal segment are pivotally connected by a pin hinge.

14. The safety shield apparatus according to claim 13, wherein the hinge is formed by cooperating elements on the proximal and distal segments.

15. The safety shield apparatus according to claim 13, wherein the retention member is integrally formed with the proximal segment.

16. The safety shield apparatus according to claim 1, wherein the proximal segment and the distal segment are manufactured as a single piece having a thinned transition region which pivotally interconnects the proximal segment and distal segment to one another.

17. The safety shield apparatus according to claim 16, wherein the retention member is also integrally formed with the proximal and distal segments.

18. The safety shield apparatus according to claim 1, wherein the safety shield apparatus is configured and adapted for use with a blood collector.

19. The safety shield apparatus according to claim 1, wherein the safety shield apparatus is configured and adapted for use with a hypodermic needle.

* * * * *